(12) United States Patent
Moribe et al.

(10) Patent No.: US 7,423,745 B2
(45) Date of Patent: Sep. 9, 2008

(54) OPTICAL INSPECTION APPARATUS AND OPTICAL INSPECTION METHOD

(75) Inventors: Hideyuki Moribe, Tokyo (JP); Motonari Tateno, Tokyo (JP)

(73) Assignee: NEC Corporation, Tokyo (JP)

( * ) Notice: Subject to any disclaimer, the term of this patent is extended or adjusted under 35 U.S.C. 154(b) by 318 days.

(21) Appl. No.: 11/230,329

(22) Filed: Sep. 20, 2005

(65) Prior Publication Data

US 2006/0066844 A1    Mar. 30, 2006

(30) Foreign Application Priority Data

Sep. 21, 2004    (JP)    ............... 2004-273295

(51) Int. Cl.
    *G01N 21/00*    (2006.01)
(52) U.S. Cl. ................. 356/237.4; 356/237.5
(58) Field of Classification Search ... 356/237.1–237.5, 356/239.1–239.3, 239.7, 239.8; 430/30
    See application file for complete search history.

(56) References Cited

U.S. PATENT DOCUMENTS 6,268,093 B1 *  7/2001  Kenan et al. ................. 430/30
6,674,522 B2 *  1/2004  Krantz et al. ............. 356/237.1
6,727,512 B2 *  4/2004  Stokowski et al. ...... 250/559.45

FOREIGN PATENT DOCUMENTS

| JP | 4-229864 | 8/1992 |
|----|----------|--------|
| JP | 6-331321 | 12/1994 |
| JP | 2002-519667 | 7/2002 |
| JP | 2002-287327 | 10/2002 |

* cited by examiner

*Primary Examiner*—Hoa Q Pham
(74) *Attorney, Agent, or Firm*—McGinn IP Law Group, PLLC

(57) ABSTRACT

An optical inspection apparatus for inspecting an inspection target surface by irradiating the inspection target surface with light, includes: a condensing and scanning optical system for condensing light from a light source on the inspection target surface in a minute spot shape and scanning the condensed minute-spot-shaped light onto the inspection target surface; and a phase change information detection apparatus for detecting optical phase change information in an area of the inspection target surface irradiated with the minute-spot-shaped light scanned by the condensing and scanning optical system.

28 Claims, 18 Drawing Sheets

OPTICAL INSPECTION APPARATUS AND OPTICAL INSPECTION METHOD

BACKGROUND OF THE INVENTION

1. Field of the Invention

The present invention relates to an optical inspection apparatus and an optical inspection method. In particular, the present invention relates to an optical inspection apparatus and an optical inspection method that are applied, for instance, to a photomask (reticle) defect inspection apparatus used at the time of transfer of a circuit pattern of a semiconductor integrated circuit or the like.

2. Description of the Related Art

Lithography techniques capable of forming finer patterns are becoming necessary following an increase of the degree of integration of semiconductor integrated circuits. Against this backdrop, various methods are proposed and realized for detecting defects of pattern shapes of photomasks used for transferring semiconductor integrated circuit patterns on a semiconductor. As the photomasks u, there are binary masks and halftone masks. The binary masks are each a mask obtained by forming a light-shielding pattern made of a metallic film or the like on a glass substrate. The halftone masks are each a mask obtained by forming a pattern made of a material, which is semitransparent with respect to an exposure wavelength, on a glass substrate.

As the lithography techniques that enable formation of finer patterns, methods using phase-shift masks are proposed. The phase-shift masks are each a photomask obtained by adding (or burying) a material (phase shifter), which shifts the phase of exposure light, onto (or into) a glass substrate. With the phase-shift masks, high-resolution exposure is made possible through interference between light passing through a portion, to which the phase shifter is added, and light passing through a portion to which the phase shifter is not added. Known examples of the phase-shift masks include halftone masks (Att-PSMs: Attenuated Phase Shift Masks) and Levenson masks (Alt-PSMs: Alternating Phase Shift Masks).

In order to expose a fine pattern using such a phase-shift mask, it is important that the phase shifter on the phase-shift mask is consistent with design data. Therefore, in recent years, defect detection techniques for photomasks, such as the phase-shift masks, are desired earnestly and various apparatuses are proposed.

For instance, as a defect detection technique for photomasks utilizing light interference, a phase-shift amount measurement method using an optical heterodyne interference method is disclosed in JP 06-331321A (1994). Also, a phase-shift mask defect inspection method using a differential interference microscope is disclosed in JP 2002-287327 A.

Further, as a method utilizing diffraction/scattering of light, a photomask inspection method using analysis of a Fourier transformation image of a uniformly illuminated phase-shift pattern is disclosed in JP 04-229864 A (1992).

Still further, a method of detecting a defect of a surface of a wafer of a reticle or integrated circuit by causing only scattered/diffracted light from a phase-shift pattern illuminated from an inclined direction to pass through a spatial filter by means of a Fourier transformation surface is disclosed in JP 2002-519667 A.

On the other hand, as a method of detecting a pattern shape defect of a binary mask for which a light-shielding pattern is formed, a halftone mask for which a semitransparent pattern is formed, or the like, there is a scanning-type microscope system. This system is a system in which a pattern formation surface of a photomask is scanned with condensed light, and the intensity of transmitted light/reflected light is detected.

However, the conventional defect detection methods for photomasks, such as phase-shift masks, have the following problems (1) to (3).

(1) With the method using an optical heterodyne interference method and the method using a differential interference microscope described above, two light beams, whose positions are slightly displaced from each other, are irradiated onto a measurement target. Then, the intensity of interference between the two light beams are measured. Therefore, there is pattern direction dependence such as difficulty of detection of patterns extending in a direction that is the same as the direction of the displacement between the two beams. Also, there are problems such as limitation of detection of pattern line widths that depend on the amount of the displacement between the two beams.

(2) Also, the method described above that uses analysis of a Fourier transformation image of a uniformly illuminated phase-shift pattern is a method with which only a phase-shift amount (phase difference, film thickness) is basically measured. Therefore, the method is not aimed at detecting minute phase defects. Also, the method is devised based on analysis of a Fourier transformation image in a general imaging system using uniform illumination like in the case of a projection exposure apparatus. Therefore, there is a problem in that it is required to uniformly illuminate two areas that are an area, in which a phase shifter is added, and an area in which no phase shifter is added.

(3) Also, the method disclosed in JP 2002-519667 A described above, with which only scattered/diffracted light from a phase-shift pattern is detected with a Fourier transformation surface, is one method that is generally used in detection of defects of semiconductor wafers and the like. That is, the method is implemented by an apparatus that detects defects by measuring and analyzing scattered/diffracted light from a region dark-field/bright-field-illuminated by a light source such as a lamp or a laser. Various forms are devised, and inmost cases, it is aimed to improve the S/N of weak scattered/diffracted light from minute defects. For the S/N improvement and defect type judgment, JP 2002-519667 A also discloses a method with which detection is performed by performing spatial filtering on diffracted light in a far-field region. However, various scattered/diffracted light occurs depending on the pattern shape and defect shape of a detection target. In order to catch as much the light as possible, some consideration is needed for the angle of illumination light, the arrangement of a light reception system (or the kind of a spatial filter), and the like. Therefore, there is a problem in that it is required to construct a complicated system with which it is possible to cope with respective kinds of defects.

The problems described above are not limited to photomasks (reticles) and also apply to inspection of electronic component substrates, for which patterns are formed, in a like manner.

SUMMARY OF THE INVENTION

In the view of foregoing and other exemplary problems, drawbacks, and disadvantages, an exemplary optical inspection apparatus of the present invention, inspects an inspection target surface by irradiating the inspection target surface with light, including: a condensing and scanning optical system for condensing light from a light source on the inspection target surface in a minute spot shape and scanning the condensed minute-spot-shaped light onto the inspection target surface;

and a phase change information detection apparatus for detecting optical phase change information in an area of the inspection target surface irradiated with the minute-spot-shaped light scanned by the condensing and scanning optical system.

An exemplary optical inspection method of the present invention, inspecting an inspection target surface by irradiating the inspection target surface with light, includes: condensing light from a light source on the inspection target surface in a minute spot shape; scanning the condensed minute-spot-shaped light onto the inspection target surface; and detecting optical phase change information in an area of the inspection target surface irradiated with the scanned minute-spot-shaped light.

As described above, according to the present invention, the condensing and scanning optical system condenses light from the light source on an inspection target surface in a minute spot shape and scans onto the inspection target surface. Then, the phase change information detection apparatus detects optical phase change information in an area of the inspection target surface irradiated with the scanned minute-spot-shaped light.

Accordingly, it is possible to identify a phase defect on the inspection target surface by comparing the detected phase change information with reference data. It is possible to perform the detection of the phase change information and the identification of the phase defect without being influenced by the direction and shape of the pattern. Therefore, the exemplary optical inspection apparatus of the present invention is an apparatus with a simple construction having a little dependence on a pattern direction and a pattern shape.

BRIEF DESCRIPTION OF THE DRAWINGS

The objects, features and advantages of the present invention will become apparent from the following detailed description when taken with the accompanying drawings in which.

DETAILED DESCRIPTION OF THE EXEMPLARY EMBODIMENTS

Now, the exemplary embodiments of the present invention will be described with reference to the accompanying drawings.

Figure 1:
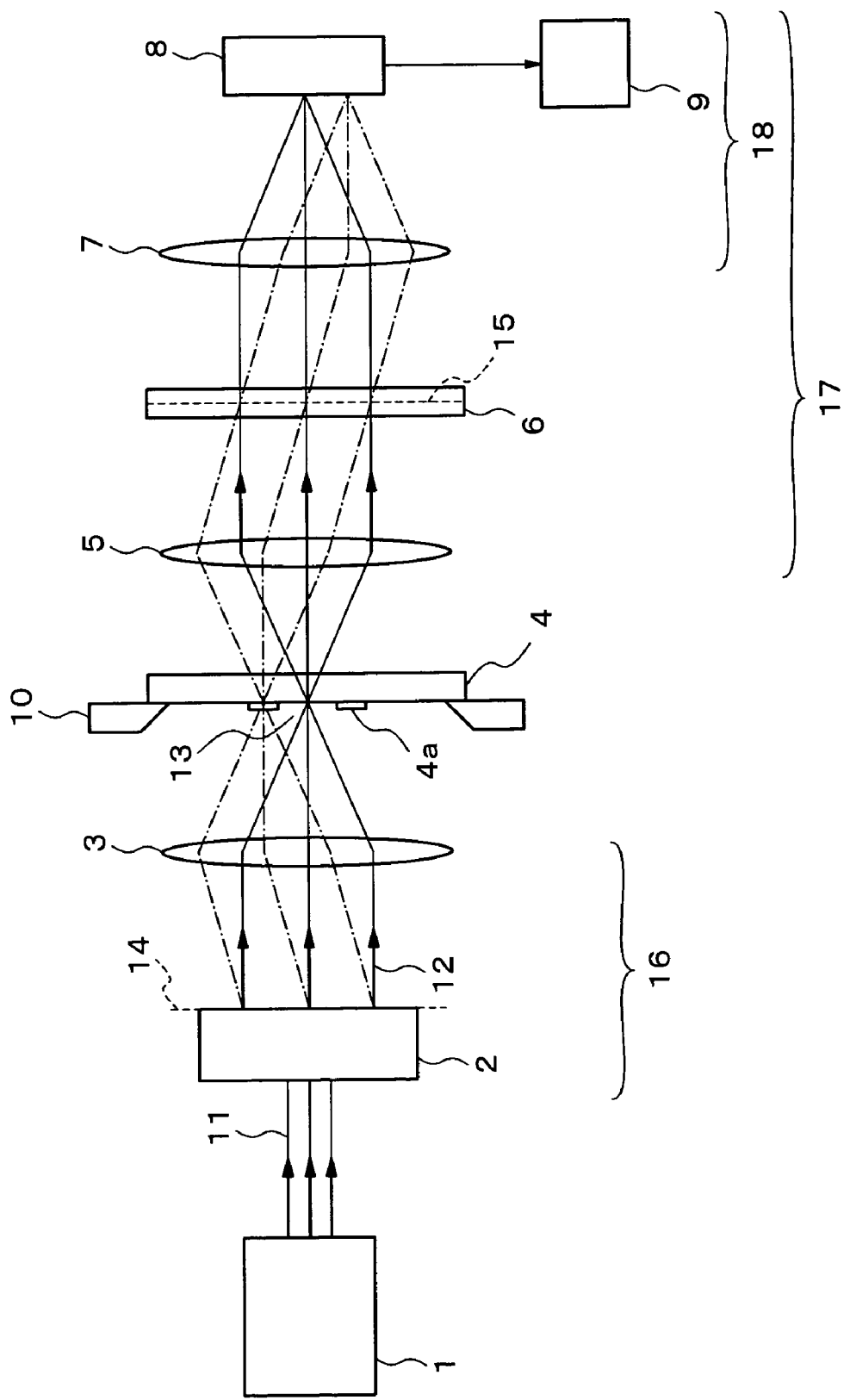
FIG. 1 shows a first exemplary embodiment of an optical inspection apparatus according to the present invention.
Figure 2:
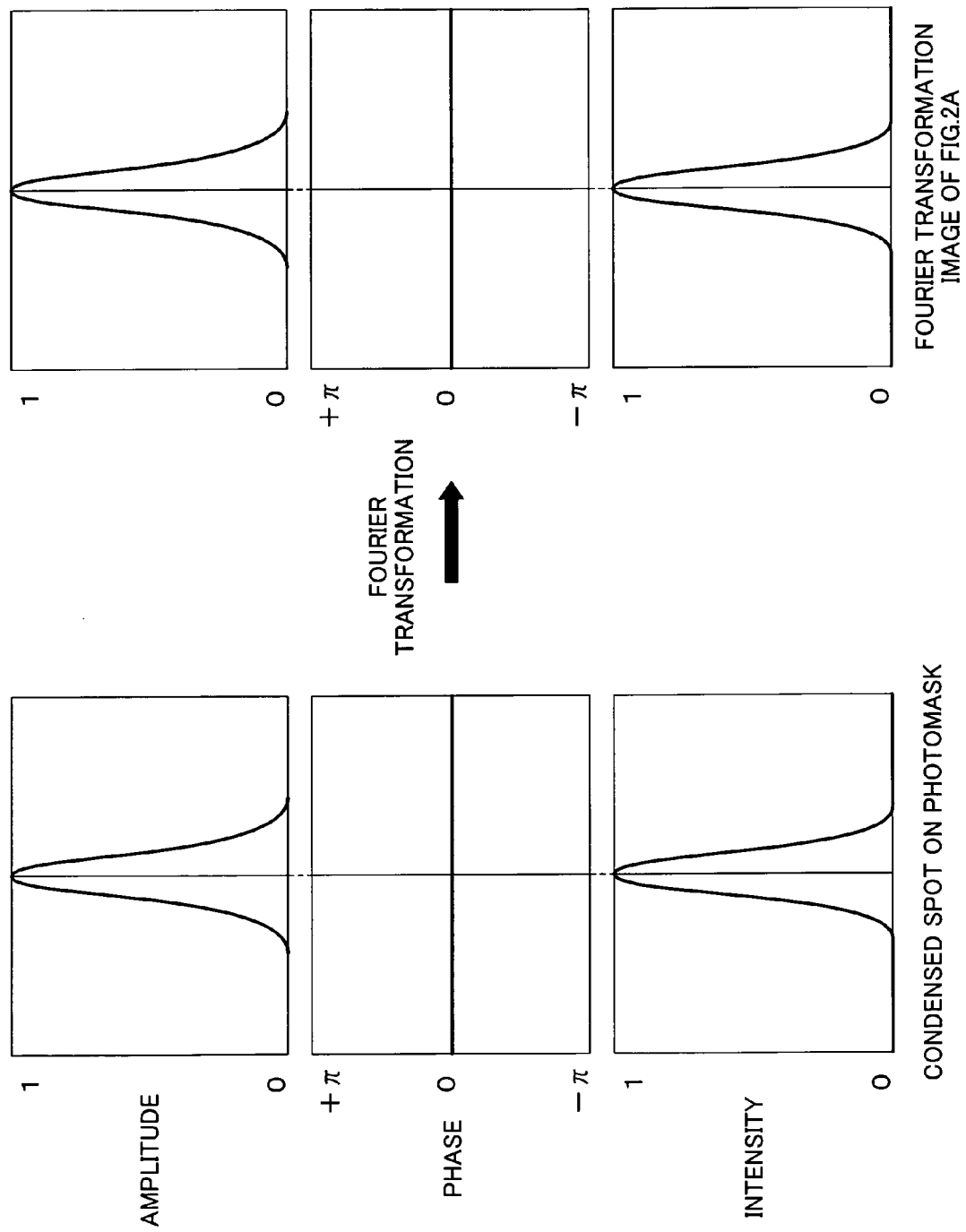
FIG. 2A shows examples of ideal spatial distributions of a condensed spot on a photomask.
FIG. 2B shows examples of calculation results of a Fourier transformation image in the case where a condensed spot having an ideal laser beam waist is irradiated onto a photomask having no pattern.
Figure 3:
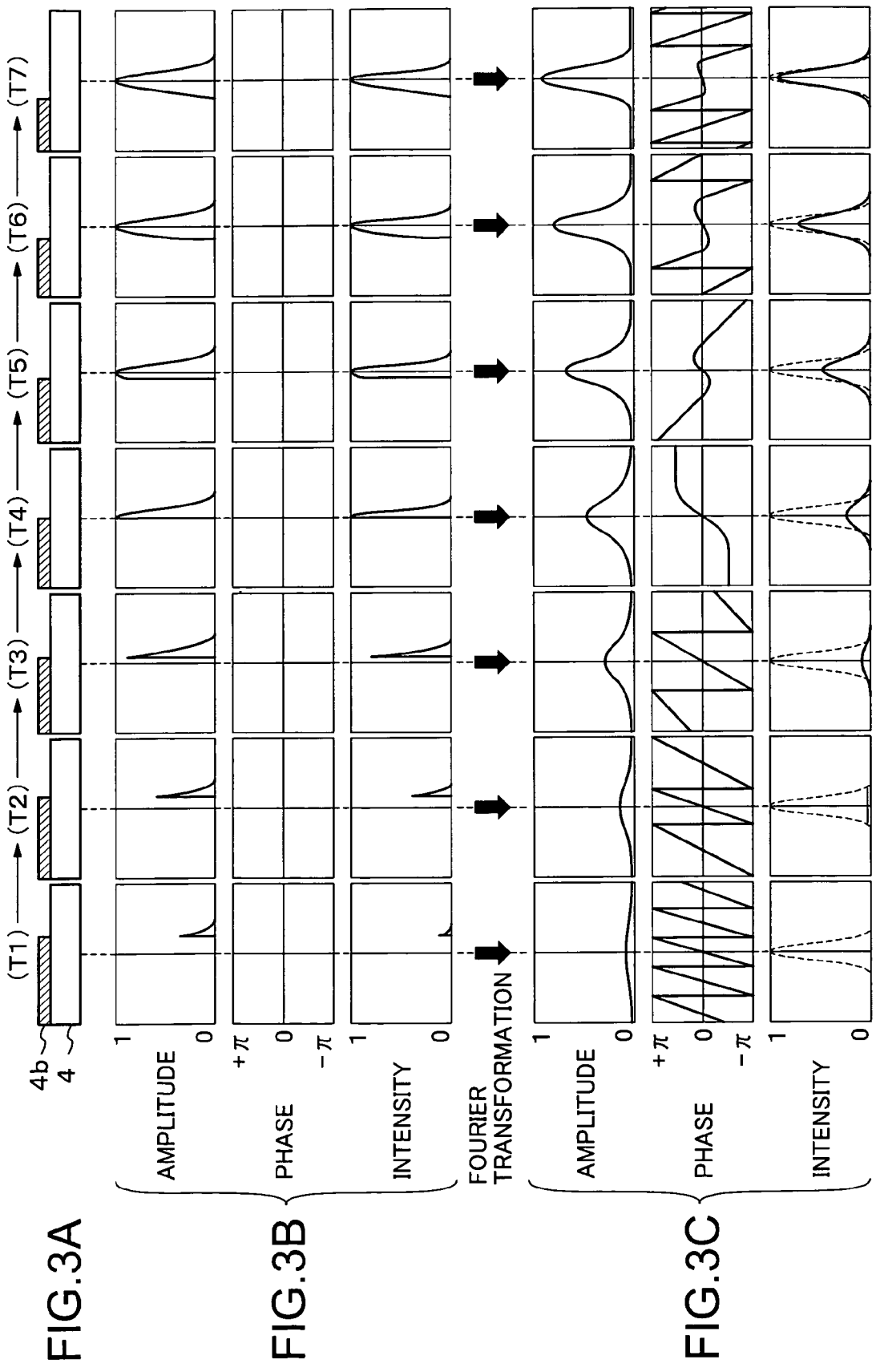
FIG. 3A shows that examples of a cross section of a photomask in the case where a photomask having a light-shielding pattern is scanned with a condensed spot having an ideal spatial distribution are arranged in a time-series manner.
FIG. 3B shows that examples of amplitude, phase, and intensity spatial distributions of light of the irradiated condensed spot immediately after the light-shielding pattern are arranged in a time-series manner.
FIG. 3C shows examples of calculation results of a Fourier transformation image corresponding to FIG. 3B.

FIG. 1 shows a first exemplary embodiment of an optical inspection apparatus according to the present invention.

Hereinafter, the following description will be made using a photomask defect detection apparatus as an example of the optical inspection apparatus.

The photomask defect detection apparatus includes a light source 1, a condensing and scanning optical system 16, a photomask 4, a phase change information detection apparatus 17, and a drive stage 10.

The condensing and scanning optical system 16 includes a scanning optical system 2 and an objective lens 3.

The phase change information detection apparatus 17 includes a collective lens 5, a spatial filter 6, and a phase change information extraction apparatus 18.

The phase change information extraction apparatus 18 includes a collective lens 7, a photoelectric transducer 8, and an image processing system 9.

The photomask defect detection apparatus inspects an inspection target surface (pattern surface of the photomask in this embodiment) using a scanning-type microscope system.

The inspection using the scanning-type microscope system means a system in which an inspection target surface is inspected by condensing and scanning light from a light source onto the inspection target surface. In the inspection using the scanning-type microscope system, it is required to reduce the diameter of a spot condensed on the inspection target surface in order to increase resolution. Therefore, a light source having a short wavelength is required. Also, a high-brightness light source is required in order to improve S/N.

Therefore, a far-ultraviolet-ray laser having a wavelength of 266 nm is used as the light source 1, for instance.

A light beam 11 emitted from the light source 1 enters the scanning optical system 2. The scanning optical system 2 converts the light beam 11 into a beam having a desired diameter, deflects the converted beam at high-speed, and emits the deflected beam as a light beam 12. As a deflection apparatus of the scanning optical system 2, a one-dimensional light deflector is used, examples of which are an acoustooptic deflector, a polygon mirror, and a galvanomirror.

The light beam 12 deflected at high speed enters the objective lens 3. The objective lens 3 has a large numerical aperture (NA) of 0.85 or the like and forms a minute condensed spot 13, whose diameter is around 0.3 to 0.4 μm, on a surface having a pattern of the photomask 4. Also, the objective lens 3 is arranged so that the starting point of deflection of the light beam 12 is placed at the front-side focal position of the lens 3. The starting point of the deflection of the light beam 12 is a pupil position 14 at which the light beam 12 swung through the deflection is superimposed on an optical axis. Therefore, the condensed spot 13 is scanned onto the photomask 4 telecentrically. Here, the "telecentric scanning on the photomask 4" means "scanning under a state where the optical axis stands vertically on the photomask 4".

The drive stage 10 holds the photomask 4 and moves it in a direction vertical to the paper plane of FIG. 1. The scanning optical system 2 scans the condensed spot 13 onto the photomask 4 in a direction along the paper plane. Therefore, the condensed spot 13 is scanned in a two-dimensional region on the photomask 4. Also, by using a two-dimensional light deflector instead of the one-dimensional light deflector, it becomes possible to scan the condensed spot 13 in the two-dimensional region only with the two-dimensional light deflector. Also, the condensed spot 13 may be scanned in the two-dimensional region by two-dimensionally moving the photomask 4 in a mechanical manner without using the light deflector.

The light beam 12 transmitting through the photomask 4 enters the collective lens 5. The collective lens 5 is arranged so that the surface having the pattern of the photomask 4 becomes the front-side focal position. Therefore, the light beam 12 transmitting through the collective lens 5 is converted into a parallel light flux. It is desirable that the collective lens 5 has a numerical aperture (NA) that is equal to or larger than that of the objective lens 3 because it is required to condense light including diffracted light by the pattern on the photomask 4.

The light beam 12 converted into the parallel light flux forms a Fourier transformation image at the rear-side focal position 15 of the collective lens 5. That is, a Fourier transformation surface of the pattern surface of the photomask 4 appears at the rear-side focal position 15. Here, the Fourier transformation image is an optical image in a Fraunhofer diffraction region (far field) in the field of optics and is an image (distribution of light) formed at the rear-side focus of a lens when an object is placed at the front-side focus of the lens. Also, the center axis of the light beam 12 (or the condensed spot 13) scanned onto the photomask 4 telecentrically crosses the optical axis at one point at the rear-side focal position 15. That is, a pupil is formed at the rear-side focal position 15.

The spatial filter 6 is set at the pupil position and performs spatial filtering about the Fourier transformation image of the pattern surface of the photomask 4 formed at the position.

The spatial filter 6 is set at the pupil position, so the same spatial filtering is performed for every beam scanning position on the photomask 4.

The light beam 12 transmitting through the spatial filter 6 is condensed by the collective lens 7 to a light reception portion of the photoelectric transducer 8. Here, the photoelectric transducer 8 uses a photodiode, a photomultiplier, or the like. The photoelectric transducer 8 converts the intensity of the light condensed by the collective lens 7 into an electric signal and sends the electric signal to the image processing system 9.

The image processing system 9 receives the electric signal from the photoelectric transducer 8 and brings the electric signal into correspondence with the scanning of the condensed spot. Then, the image processing system 9 generates the shape of the two-dimensional pattern on the photomask as an image by two-dimensional scanning positions and values of the electric signal corresponding to the positions.

When not detecting a phase defect on the photomask 4 but detecting a light-shielding/semitransparent pattern shape defect, the spatial filter 6 is removed from the construction shown in FIG. 1. That is, the light beam 12 transmitting through the collective lens 5 and converted into the parallel light flux is guided to the collective lens 7 without being spatially filtered. Other points are the same as those in the case of detection of a phase defect on the photomask 4.

Next, an operation of the optical inspection apparatus (photomask defect detection apparatus) in this embodiment will be described in detail with reference to FIGS. 2A to 17 in the order from A to E given below.

A. First, the condensed spot 13 on the photomask 4 will be described.

B. Next, detection of the light-shielding/semitransparent pattern shape on the photomask 4 will be described.

C. Next, detection of a phase defect on the photomask 4 will be described using theoretical calculation.

D. Next, detection of a phase defect on the photomask 4 using experimental results and identification of the phase defect will be described.

E. Finally, a case where another spatial filter is used will be described.

Here, the phase defect means a defect that causes no difference in transmittance with respect to inspection light (light of the condensed spot 13) and changes only the phase of the light.

A. First, the condensed spot 13 on the photomask 4 will be described.

FIG. 2A shows examples of ideal spatial distributions of the condensed spot 13 on the photomask 4 and shows the amplitude, phase, and light intensity spatial distributions of the condensed spot 13 having an ideal laser beam waist. The condensed spot having an ideal laser beam waist means a condensed spot having a perfect Gaussian amplitude distribution and a planar phase distribution. In this embodiment, it is assumed that a beam having a perfect Gaussian amplitude distribution and a planar phase distribution is condensed on the photomask 4.

FIG. 2B shows examples of calculation results of a Fourier transformation image in the case where the condensed spot 13 having an ideal laser beam waist is irradiated onto the photomask 4 having no pattern. The amplitude, phase, and light intensity of the Fourier transformation image are shown in this order from the top. The photomask 4 is a transparent glass or the like having no pattern. The Fourier transformation image is a Fourier transformation image of a surface of the photomask 4 having no pattern and is an image generated at the rear-side focal position 15 of the collective lens 5.

The actual size of the condensed spot 13 shown in FIG. 2A is of the order of μm on the photomask 4. The actual size of the Fourier transformation image shown in FIG. 2B is of the order of mm at the rear-side focal position 15. The sizes greatly differ from each other, but illustration is made by arbitrarily setting spatial scales (horizontal axes) in the drawings.

B. Next, detection of the light-shielding/semitransparent pattern shape on the photomask 4 will be described with reference to FIGS. 3A to 4.

FIG. 3A shows examples of a cross section of the photomask 4 in the case where a light-shielding pattern 4b of a binary mask or the like is scanned with the condensed spot 13 having the spatial distributions shown in FIG. 2A. In the drawing, states, in which the light-shielding pattern 4b relatively moves following the scanning of the condensed spot 13, are arranged in a horizontal direction in a time-series manner in the order from (T1) to (T7).

FIG. 3B shows examples of the amplitude, phase, and intensity spatial distributions of the light of the irradiated condensed spot 13 immediately after the light-shielding pattern 4b (immediately after the light-shielding pattern 4b surface of the photomask 4). In the drawing, states, in which the amplitude, phase, and intensity spatial distributions change following the scanning of the condensed spot 13, are arranged in the horizontal direction in a time-series manner in the order from (T1) to (T7).

FIG. 3C shows examples of calculation results of a Fourier transformation image corresponding to FIG. 3B. Note that in the figures of Fourier transformation image intensity (light intensity) in FIG. 3C, a distribution in the case where the light-shielding pattern 4b does not exist (FIG. 2B) is superimposedly displayed with a broken line. In the drawing, like in FIGS. 3A and 3B, states, in which the Fourier transformation image changes following the scanning of the condensed spot 13, are arranged in a time-series manner in the order from (T1) to (T7).

The photoelectric transducer 8 receives each light distribution respectively that changes in a time-series manner from (T1) to (T7) in FIG. 3C with the light reception surface of the photoelectric transducer 8. Then, the photoelectric transducer 8 integrates each received light distribution respectively and converts each result of the integration into a light intensity signal respectively.

It should be noted here that in the case of detection of a light-shielding/semitransparent pattern shape, the spatial filter 6 shown in FIG. 1 is not provided. Also, it is assumed that light of the Fourier transformation image in FIG. 3C is received by the photoelectric transducer 8 through the collective lens 7 as it is and is converted into an electric signal.

Figure 4:
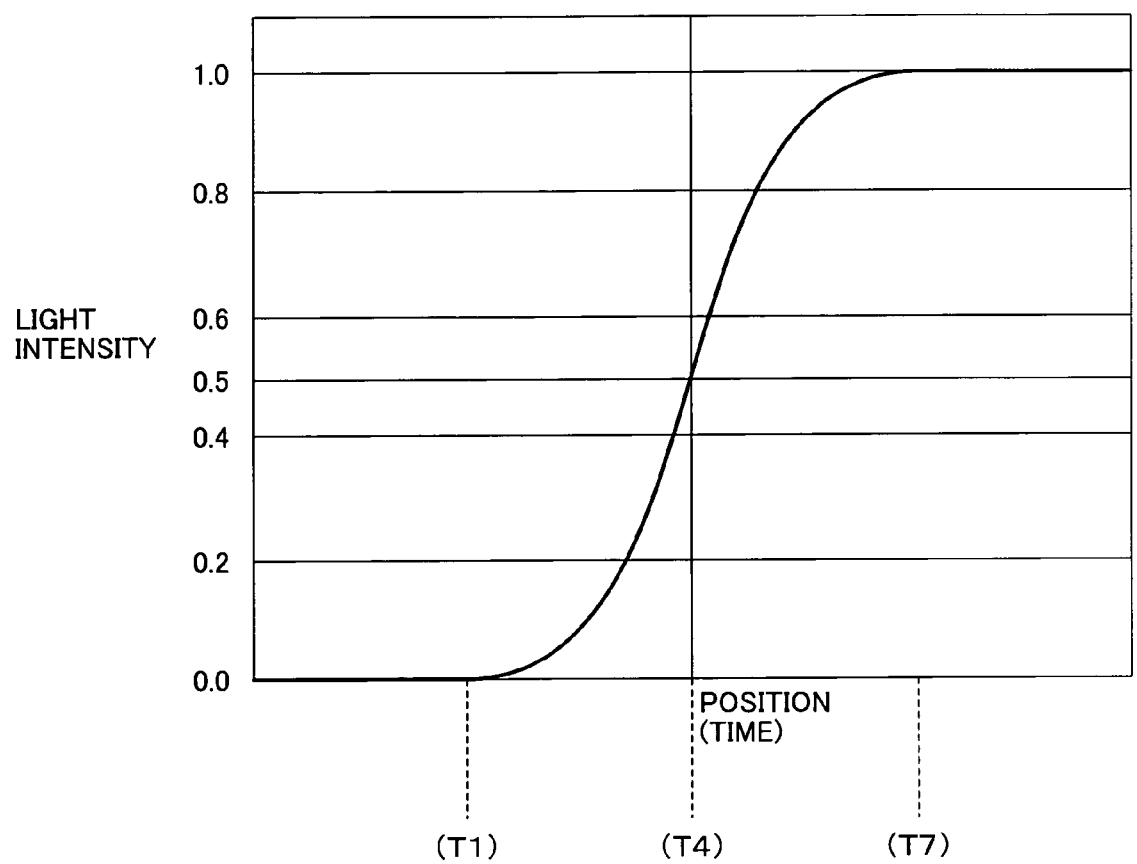
FIG. 4 shows an example of a relation between a light intensity signal and a condensed spot scanning position (in the case of a light-shielding pattern with no spatial filter)

FIG. 4 shows an example of a relation between the light intensity signal and the scanning position of the condensed spot 13 in the case where the light-shielding pattern shape is detected without providing the spatial filter 6.

The image processing system 9 receives the light intensity signal from the photoelectric transducer 8, brings the light intensity signal into correspondence with the scanning position of the condensed spot 13, creates an image shown in FIG. 4, and stores its data. FIG. 4 shows changing of the light intensity shown in FIG. 3C, with the horizontal axis representing the position (time). Symbols (T1), (T4), and (T7) are given to portions of the horizontal axis corresponding to the symbols (T1), (T4), and (T7) indicating the time series in FIGS. 3A to 3C. An edge position of the light-shielding pattern is obtained as a position at which the light intensity becomes ½.

Then, by two-dimensionally scanning the condensed spot 13 onto the pattern surface on the photomask, the pattern shape on the photomask, such as a binary mask, is detected. That is, the image processing system 9 brings the light intensity signal from the photoelectric transducer 8 and the scanning position of the condensed spot 13 at the time of the two-dimensional scanning into correspondence with each other. Then, the image processing system 9 generates the shape of the two-dimensional pattern on the photomask as an image based on two-dimensional scanning positions and light intensity signals corresponding to the positions.

C. Next, detection of a phase defect on the photomask 4 will be described using theoretical calculation with reference to FIGS. 5A to 12.

FIGS. 5A and 6A are each a drawing in which examples of a cross section of the photomask 4 in the case where a phase defect 4a on the photomask, such as a phase-shift mask, is scanned with the condensed spot 13 having the spatial distributions shown in FIG. 2A are arranged in a time-series manner.

It should be noted here that FIG. 5A relates to a case where the phase defect 4a causes a phase shift of λ/2 (180°). Here, λ is the wavelength of the inspection light (condensed spot 13). Also, FIG. 6A relates to a case where the phase defect 4a causes a phase shift of λ/4 (90°).

FIGS. 5A and 6A each show that states, in which the phase defect 4a relatively moves following the scanning of the condensed spot 13, are arranged in a horizontal direction in a time-series manner in the order from (T1) to (T7).

FIGS. 5B and 6B each show that examples of the amplitude absolute value, phase, and intensity spatial distributions of the light of the irradiated condensed spot 13 immediately after the phase defect 4a are arranged in a time-series manner. In those drawings, states, in which the amplitude, phase, and intensity spatial distributions change following the scanning of the condensed spot 13, are arranged in the horizontal direction in a time-series manner in the order from (T1) to (T7).

FIGS. 5C and 6C each show examples of calculation results of a Fourier transformation image corresponding to FIGS. 5B and 6B, respectively. Note that in the figures of Fourier transformation image light intensity in FIGS. 5C and 6C, a distribution in the case where the phase defect 4a does not exist (FIG. 2B) is superimposedly displayed with a broken line. In FIGS. 5C and 6C, like in FIGS. 5A and 5B, and 6A and 6B, respectively, states, in which the Fourier transformation image changes following the scanning of the condensed spot 13, are arranged in a time-series manner in the order from (T1) to (T7).

Figure 5:
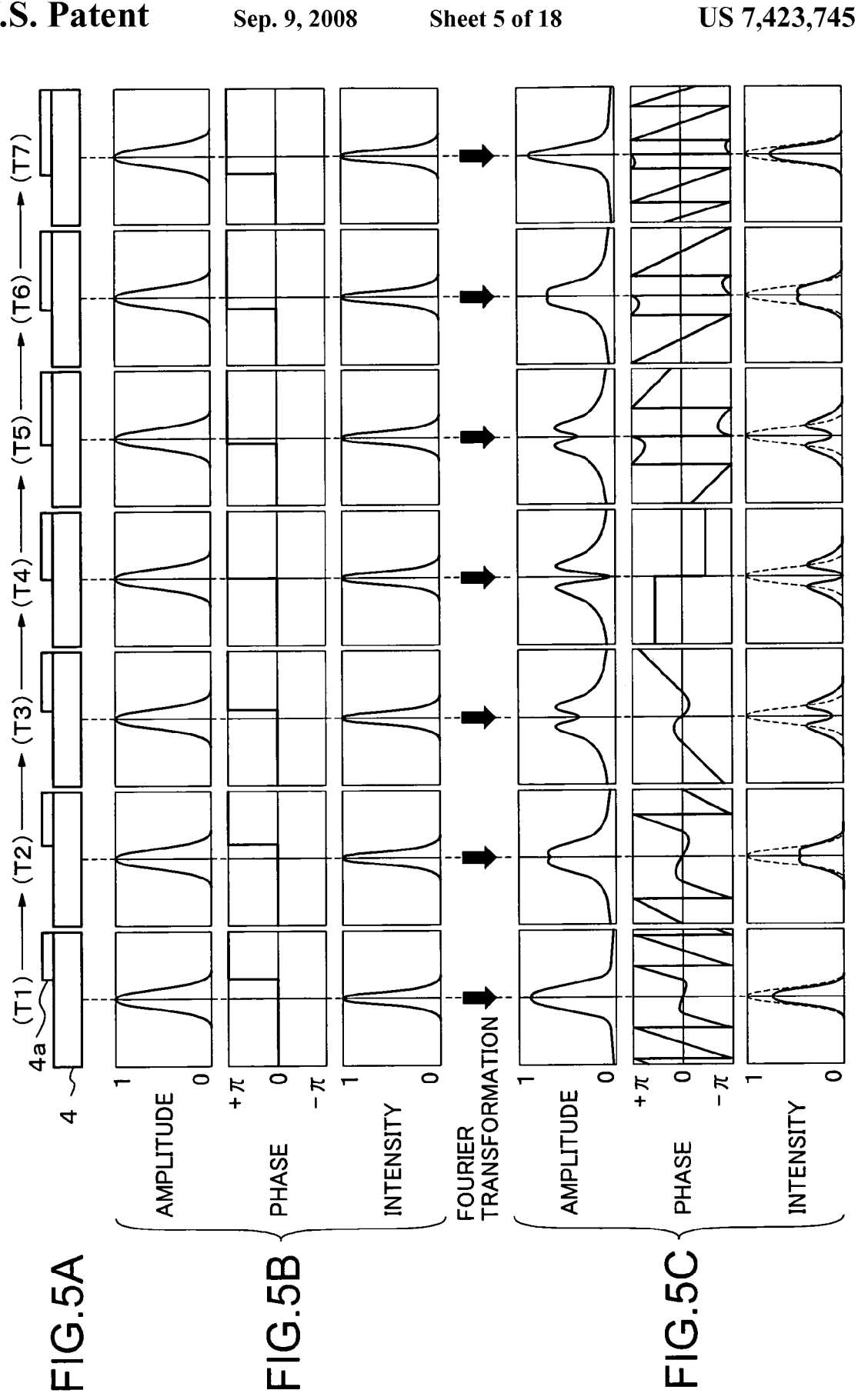
FIG. 5A shows that examples of a cross section of a photomask in the case where a photomask having a phase defect is scanned with a condensed spot having an ideal spatial distribution are arranged in a time-series manner.
FIG. 5B shows that examples of amplitude absolute value, phase, and intensity spatial distributions of light of the irradiated condensed spot immediately after the phase defect are arranged in a time-series manner.
FIG. 5C shows examples of calculation results of a Fourier transformation image corresponding to FIG. 5B.
Figure 6:
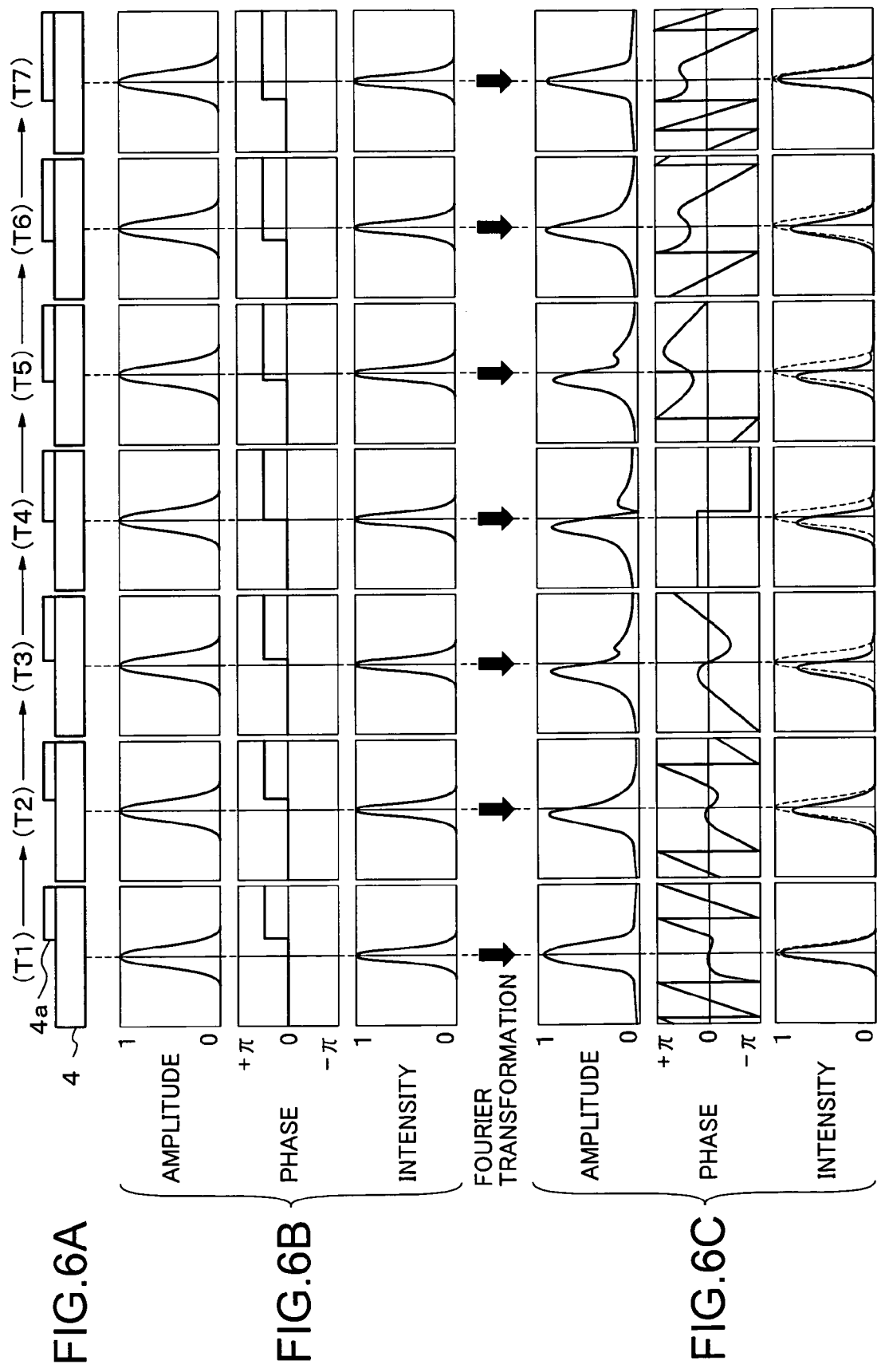
FIG. 6A shows that other examples of the cross section of the photomask in the case where the photomask having the phase defect is scanned with the condensed spot having the ideal spatial distribution are arranged in a time-series manner.
FIG. 6B shows that other examples of the amplitude absolute value, phase, and intensity spatial distributions of the light of the irradiated condensed spot immediately after the phase defect are arranged in a time-series manner.
FIG. 6C shows examples of calculation results of a Fourier transformation image corresponding to FIG. 6B.
Figure 7:
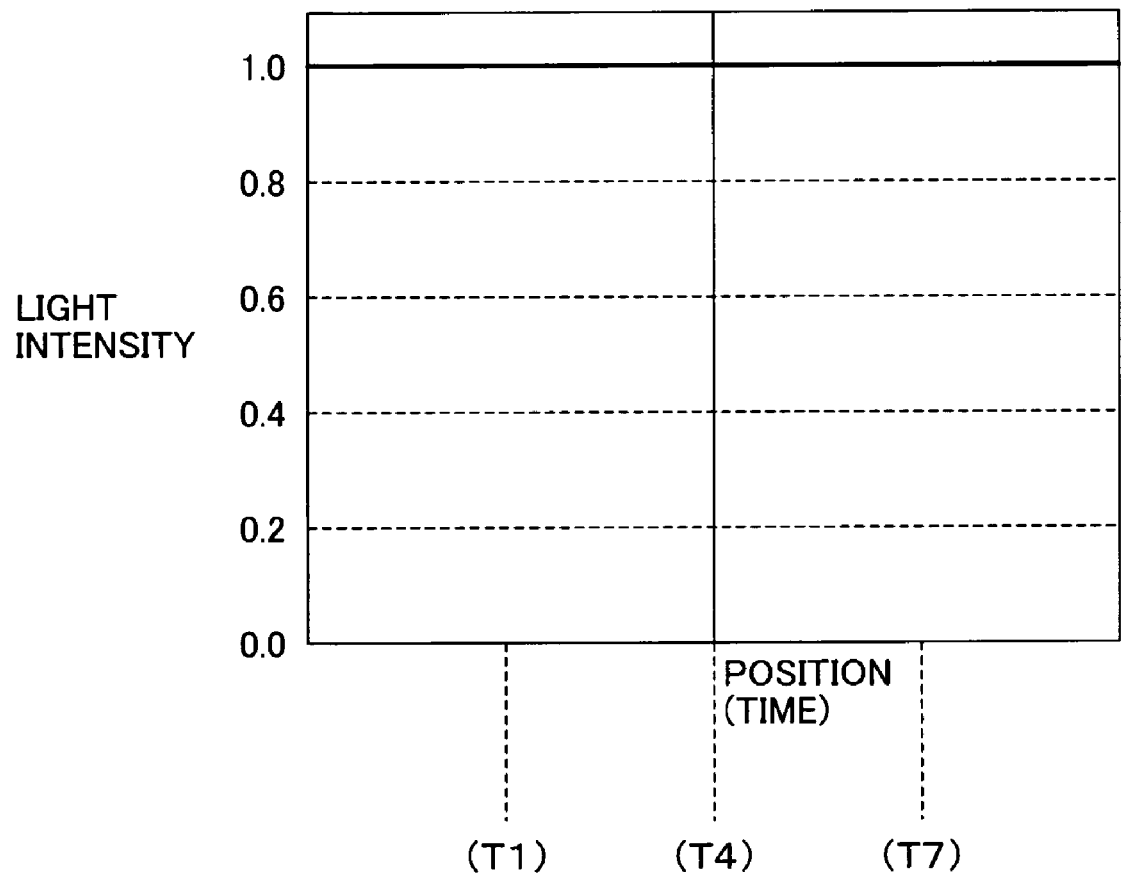
FIG. 7 shows an example of a relation between a light intensity signal and a condensed spot scanning position (in the case of a phase defect with no spatial filter)
Figure 8:
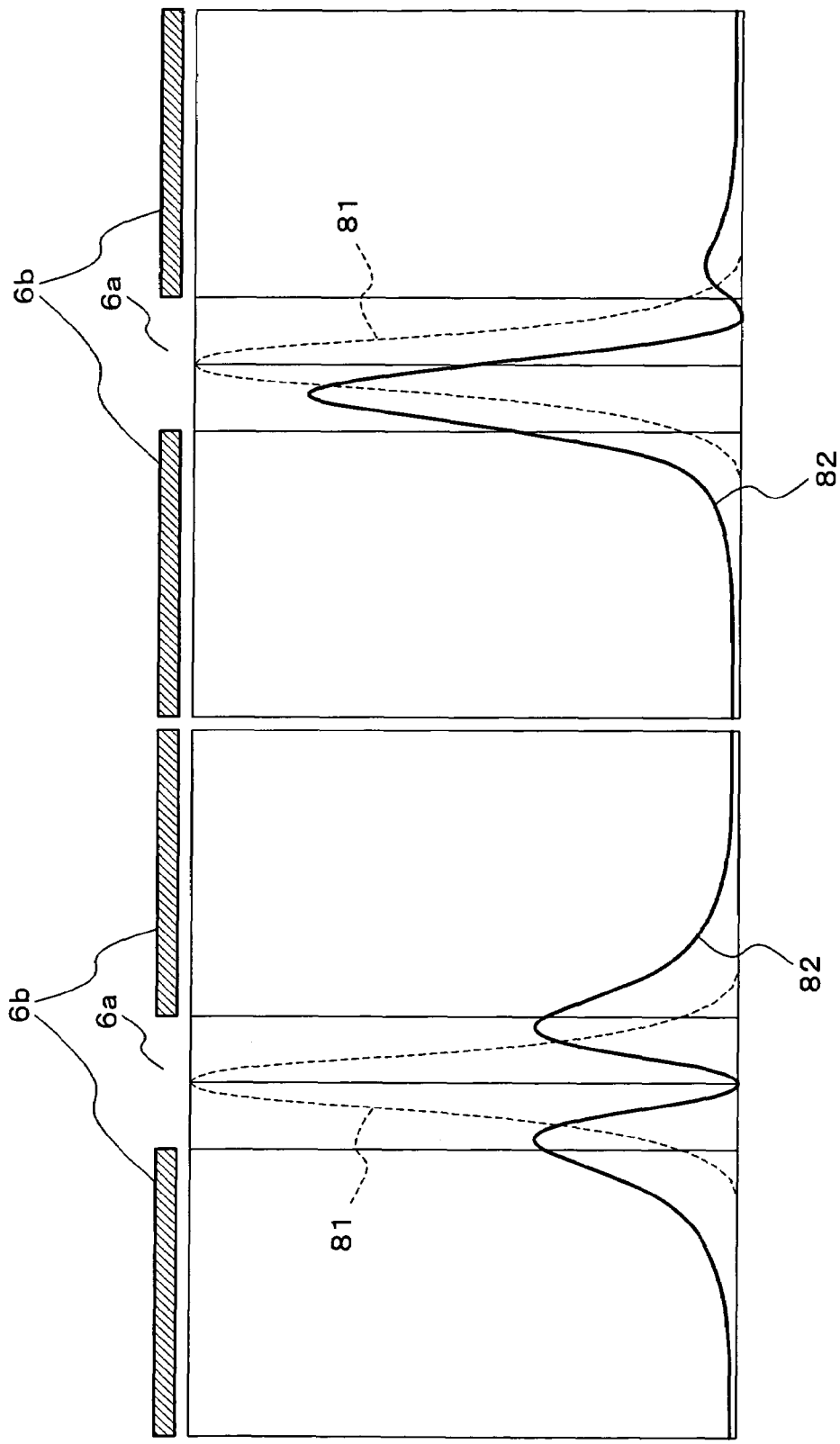
FIG. 8A shows an example of an intensity distribution of a Fourier transformation image in the case where an edge portion of a phase defect is positioned at the center of a condensed spot (in the case where a phase-shift amount is 180°)
FIG. 8B shows an example of an intensity distribution of a Fourier transformation image in the case where an edge portion of a phase defect is positioned at the center of a condensed spot (in the case where a phase-shift amount is 90°)

FIG. 7 corresponds to FIG. 4 and shows an example of changing of the light intensity shown in FIGS. 5C and 6C. The horizontal axis represents the position (time). Symbols (T1), (T4), and (T7) are given to portions of the horizontal axis corresponding to the symbols (T1), (T4), and (T7) indicating the time series in FIGS. 5A to 6C.

Like in the case of FIG. 4, it is assumed that the spatial filter 6 shown in FIG. 1 is not provided and the light of the Fourier transformation image in FIGS. 5C and 6C is received by the photoelectric transducer 8 through the collective lens 7 as it is and is converted into an electric signal.

In this case, as shown in FIG. 7, there is no changing of the light intensity corresponding to the scanning position of the condensed spot 13 (there is no changing of light transmittance). Therefore, the phase defect 4a is not detected. Here, the calculation result in FIG. 7 is obtained by assuming an optical system having an infinitely large aperture with which no "optical eclipse" occurs. In reality, however, the aperture of the optical system is limited and it is impossible to catch every scattered light generated by the edge of the phase defect 4a, so a minute light quantity reduction is detected.

FIG. 8A shows only a part of the light intensity distribution in FIG. 5C corresponding to the case where the edge portion of the phase defect 4a is positioned at the center of the condensed spot 13. Therefore, FIG. 8A shows the intensity distribution of the Fourier transformation image in FIG. 5C in the case where the phase-shift amount $\Delta\Phi$ is $\lambda/2$ and corresponds to the figure given the symbol (T4) indicating the time series. In the drawing, a translucent portion 6a and a light-shielding portion 6b of the spatial filter 6 are also illustrated.

FIG. 8B shows only a part of the light intensity distribution in FIG. 6C corresponding to the case where the edge portion of the phase defect 4a is positioned at the center of the condensed spot 13. Therefore, FIG. 8B shows the intensity distribution of the Fourier transformation image in FIG. 6C in the case where the phase-shift amount $\Delta\Phi$ is $\lambda/4$ and corresponds to the figure given the symbol (T4) indicating the time series. In the drawing, a translucent portion 6a and a light-shielding portion 6b of the spatial filter 6 are also illustrated.

Compared with the light intensity distribution 81 in the case where the phase defect 4a does not exist, the light intensity distribution 82 in the case where the phase defect 4a exists significantly changes both in FIGS. 8A and 8B. As can be seen from the drawings, the light intensity immediately after transmitting through the phase defect 4a (light intensity in FIGS. 5B and 6B) does not change, so detection of the phase defect 4a based on the light intensity is impossible. In the Fourier transformation image, however, information of the phase defect 4a appears as the light intensity distribution (FIG. 5C, FIG. 6C). Therefore, detection of the phase defect 4a based on the light intensity distribution of the Fourier transformation image is possible.

Here, the spatial filter 6 for effectively extracting the information of the phase defect 4a that appears as the light intensity distribution of the Fourier transformation image is determined based on a result of the theoretical calculation described above.

The spatial filter 6 is set at the rear-side focal position 15 on which the Fourier transformation image is formed.

The spatial filter 6 is a filter which effectively produces a difference between the light intensities resulting from the filtering using the filter in cases of the light intensity distribution 81 of the Fourier transformation image without the phase defect 4a and of the light intensity distribution 82 of the Fourier transformation image with the phase defect 4a.

That is, the spatial filter 6 had better be able to extract a large difference between the light intensity of the Fourier transformation image at an edge of an area (phase defect 4a) having property for causing a phase change, and the light intensity of the Fourier transformation image in an area not having such property.

Figure 9:
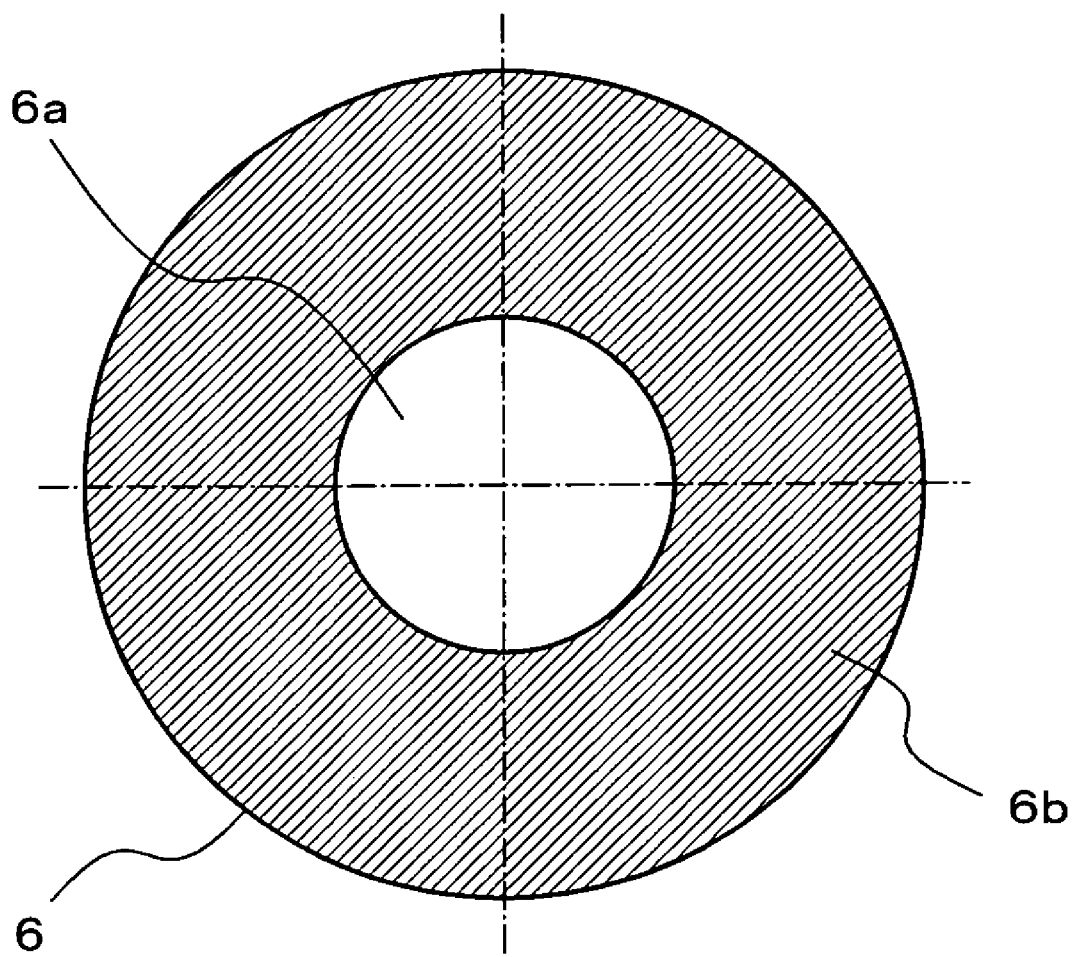
FIG. 9 shows an example of a spatial filter that transmits light in a center portion and shields light in a peripheral portion.

For instance, the spatial filter 6 shown in FIG. 9 is conceivable which transmits light in the center portion of the pupil existing at the rear-side focal position 15 of the collective lens 5 and shields light in the peripheral portion thereof. With the spatial filter 6, light corresponding to the translucent portion 6a in FIGS. 8A and 8B is transmitted. In the translucent portion 6a, a difference is large between the light intensity distribution 81 of the Fourier transformation image without the phase defect 4a and the light intensity distribution 82 of the Fourier transformation image with the phase defect 4a. Therefore, the spatial filter 6 is effective for producing a difference between the light intensities of the Fourier transformation in the cases where the phase defect 4a does not exist and where the phase defect 4a exists.

Figure 10:
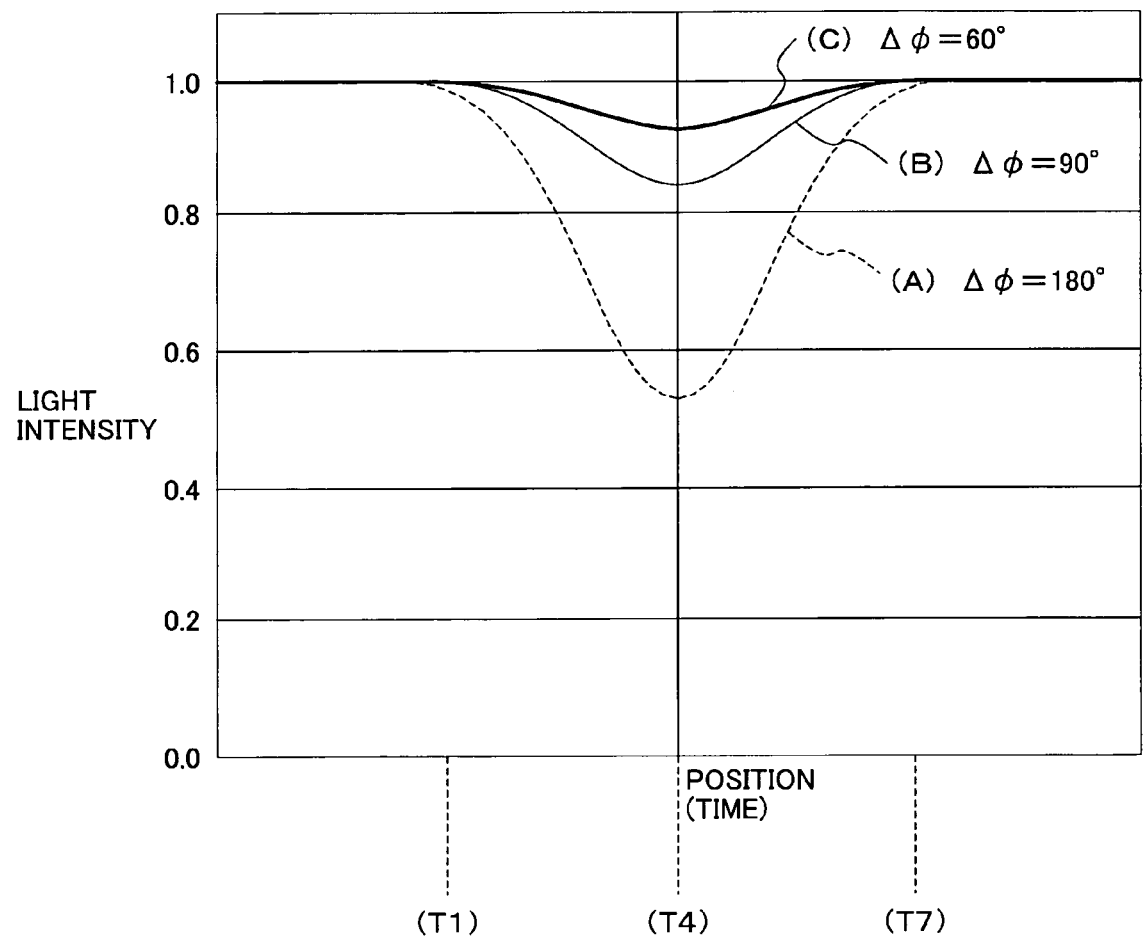
FIG. 10 shows an example of a relation between a light intensity signal and a condensed spot scanning position (in the case of a phase defect with a spatial filter)
Figure 11:
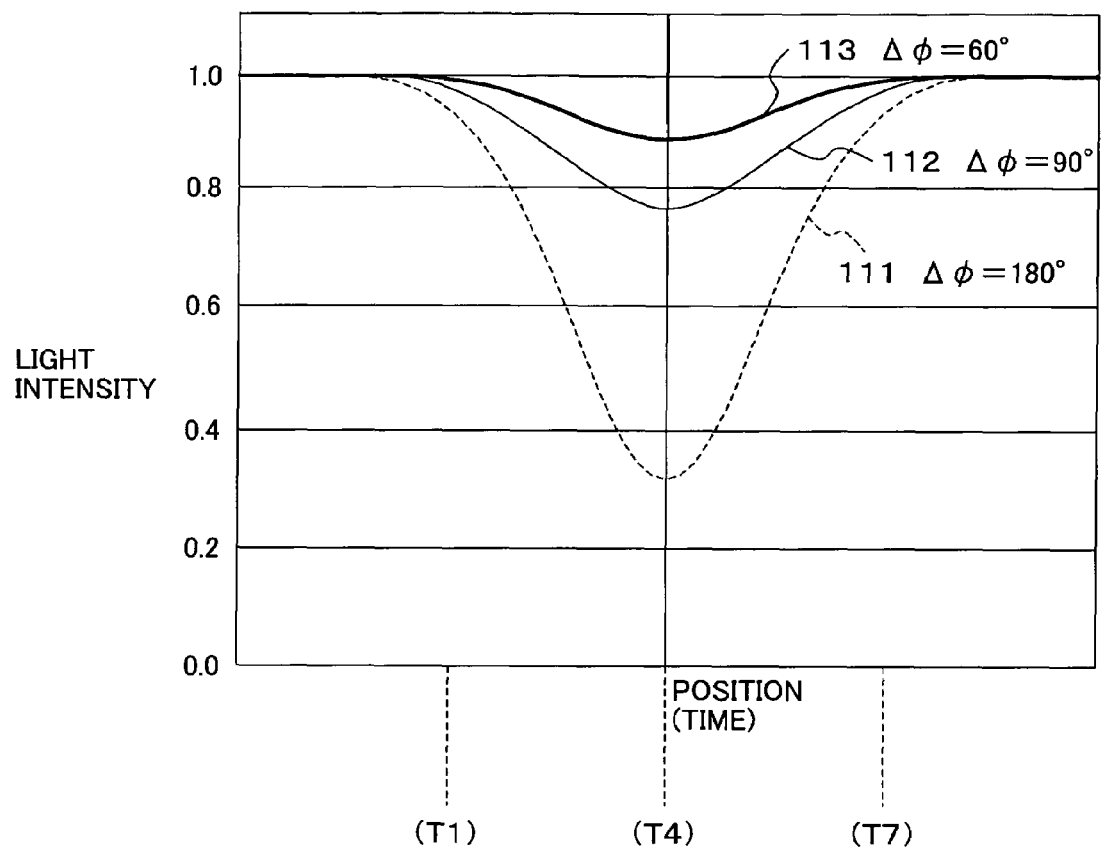
FIG. 11 shows another example of the relation between the light intensity signal and the condensed spot scanning position (in the case of the phase defect with the spatial filter)

Calculation results of time changes of the signal obtained by the photoelectric transducer 8 in the case where the spatial filter 6 shown in FIG. 9 is set at the pupil position existing at the rear-side focus of the collective lens 5 are shown in FIGS. 10 and 11. FIGS. 10 and 11 show changing of the light intensity shown in FIGS. 5C and 6C in the case where the spatial filter 6 shown in FIG. 9 is used, with the horizontal axis representing the position (time). Symbols (T1), (T4), and (T7) are given to portions of the horizontal axis corresponding to symbols (T1), (T4), and (T7) indicating the time series in FIGS. 5A to 6C.

FIGS. 10 and 11 both show calculation results on the calculation conditions that the wavelength of the inspection light and the design wavelength of the phase shifter are respectively set to 266 nm and 193 nm that corresponds to the oscillation wavelength of the ArF laser. Also, three kinds of phase-shift amounts of 180°, 90°, and 600 are used.

FIG. 10 shows calculation results obtained in the case where there is provided the spatial filter 6 having an aperture diameter corresponding to the "1/(e×e) beam diameter" (light quantity is 86.5%) of the Gaussian distribution without the phase defect 4a. Here, the Gaussian distribution in the case where the phase defect 4a does not exist corresponds to the light intensity distribution 81 of the Fourier transformation image in each of FIGS. 8A and 8B. In FIG. 10, reference symbol (A) denotes a calculation result in the case where the phase-shift amount $\Delta\Phi$ is 180°, reference symbol (B) denotes a calculation result in the case where the phase-shift amount $\Delta\Phi$ is 90°, and reference symbol (C) denotes a calculation result in the case where the phase-shift amount $\Delta\Phi$ is 60°.

FIG. 11 shows calculation results in the case where the aperture diameter is set smaller than that in FIG. 10. In FIG. 11, reference symbol (A) denotes a calculation result in the case where the phase-shift amount $\Delta\Phi$ is 180°, reference symbol (B) denotes a calculation result in the case where the phase-shift amount ΔΦ is 90°, and reference symbol (C) denotes a calculation result in the case where the phase-shift amount ΔΦ is 60°.

In the calculation results in FIGS. 10 and 11, the light intensity is significantly lowered in the edge portion, of the phase defect 4a. On the other hand, in FIG. 7 showing the calculation results in the case where the spatial filter 6 does not exist, there is no changing even in the edge portion of the phase defect 4a and the light intensity remains constant. Therefore, by setting the spatial filter 6 at the pupil position and detecting the lowering of the light intensity shown in FIGS. 10 and 11, it becomes possible to detect the phase change given by the phase defect 4a to the light beam 12 as changing of the light intensity.

Figure 12:
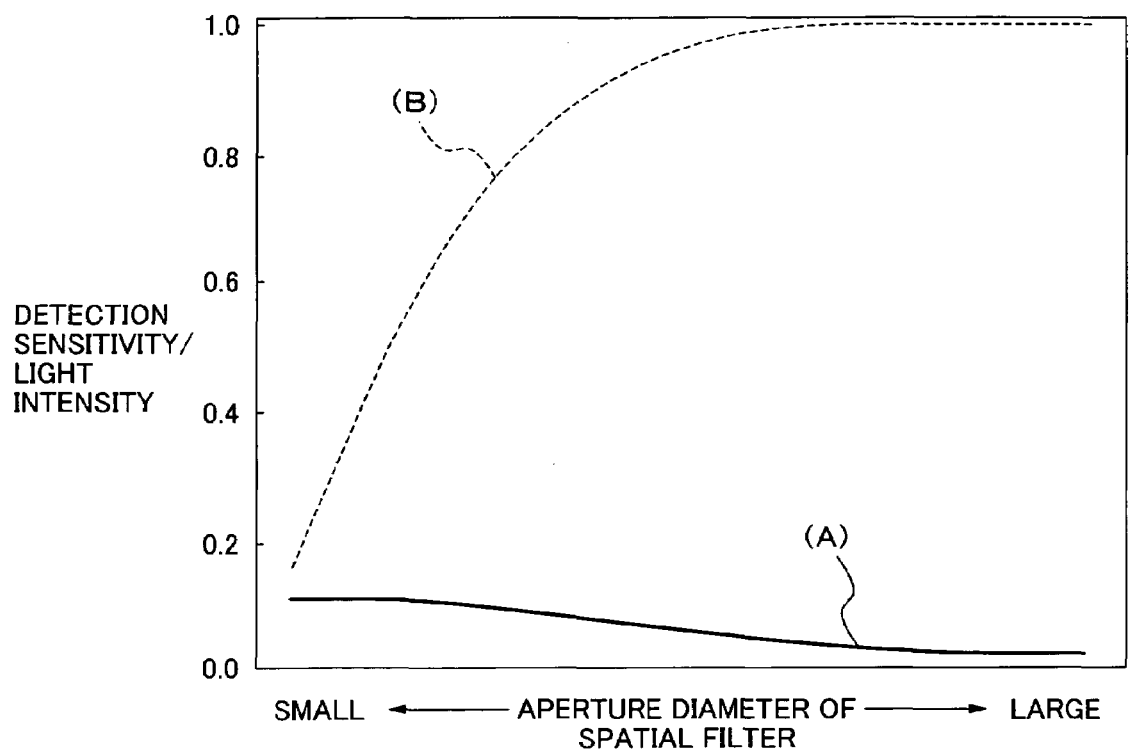
FIG. 12 shows an example of a relation of a detection signal peak value to an aperture diameter of a spatial filter in the case of a phase-shift amount of 60°.

FIG. 12 shows a result of calculation for obtaining a relation between a detection signal peak value (A) (corresponding to detection sensitivity in the drawing) and the aperture diameter of the spatial filter 6 in the case where the phase-shift amount ΔΦ is 60°. The detection signal peak value (A) is a value corresponding to a light intensity lowering peak value in FIGS. 10 and 11. In addition, there is also illustrated a relation between a transmitted light quantity (B) (corresponding to light intensity in the drawing) under a state, in which there is no phase pattern such as a phase defect or a phase shifter, and the aperture diameter of the spatial filter 6.

FIG. 12 indicates that as the aperture diameter is reduced, the detection sensitivity is improved but the transmitted light quantity is reduced. Accordingly, as the aperture diameter is reduced, S/N is deteriorated. Therefore, it is required to select an optimum value of the aperture diameter in a range in which no significant influence is exerted on S/N.

D. Next, detection of a phase defect on the photomask 4 using experimental results and identification of the phase defect will be described with reference to FIGS. 13A to 15B.

In the above description, the photomask defect detection apparatus according to the present invention has been explained based on the theoretical calculation. Next, experimental results will be described below and effectiveness of the photomask defect detection apparatus according to the present invention will be proved using FIGS. 13A to 15B.

First, an experimental result in the case where the spatial filter 6 is not provided in the photomask defect detection apparatus shown in FIG. 1 will be described.

FIGS. 13A to 14B each show an example of the experimental result in the case where the spatial filter 6 is not provided in the construction of the optical inspection apparatus (photomask defect detection apparatus) shown in FIG. 1.

Figure 13A:
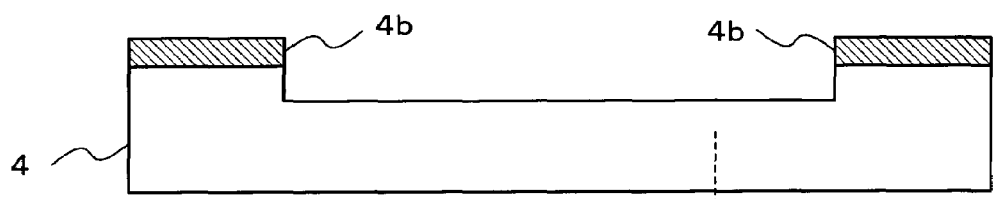
FIG. 13A shows an example of a cross section of a photomask having a construction in which a light-shielding pattern is formed on a substrate.
Figure 13B:
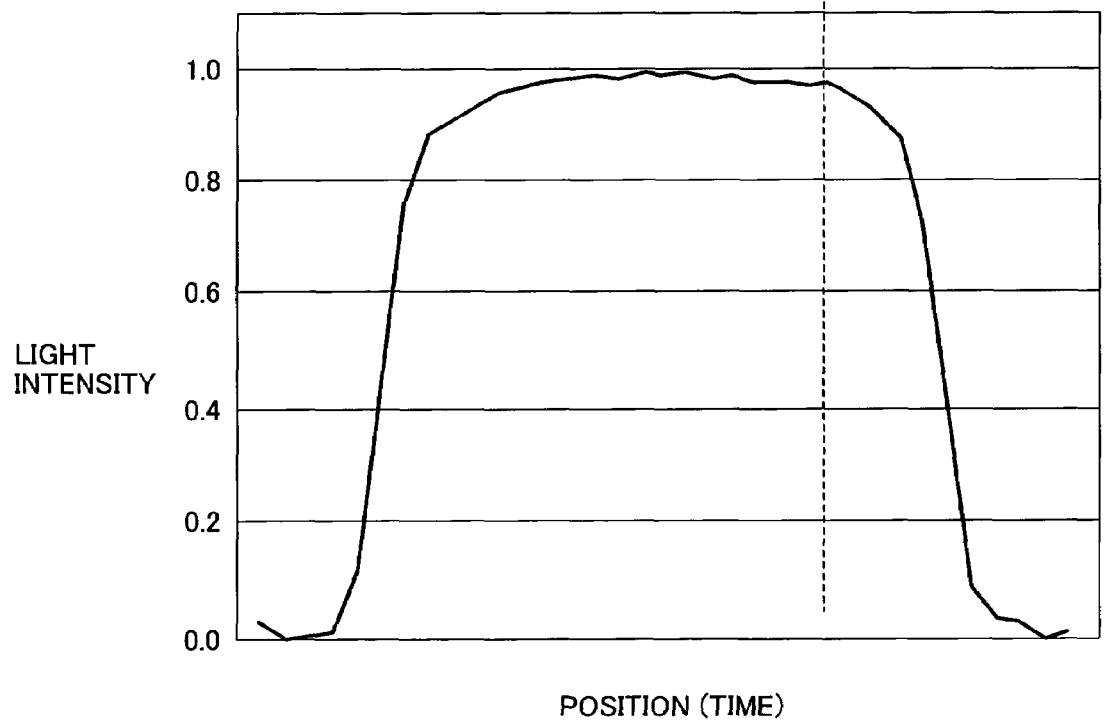
FIG. 13B shows an example of an output result of an image processing system in the case where the photomask shown in FIG. 13A is applied to a photomask defect detection apparatus in which no spatial filter is provided.

FIG. 13A shows an example of a cross-section of the photomask 4 having a construction in which a light-shielding pattern 4b is formed on a substrate, such as a glass substrate, which transmits light. FIG. 13B shows an output result of the image processing system 9 in the case where the photomask 4 shown in FIG. 13A is applied to the photomask defect detection apparatus in which the spatial filter 6 is not provided.

Figure 14A:
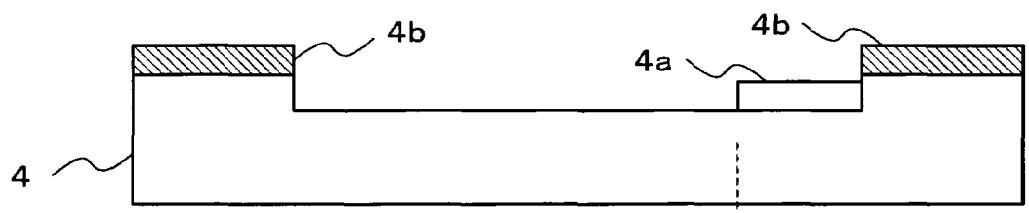
FIG. 14A shows an example of a cross section of a photomask having a construction in which a phase defect is added to the photomask shown in FIG. 13A.
Figure 14B:
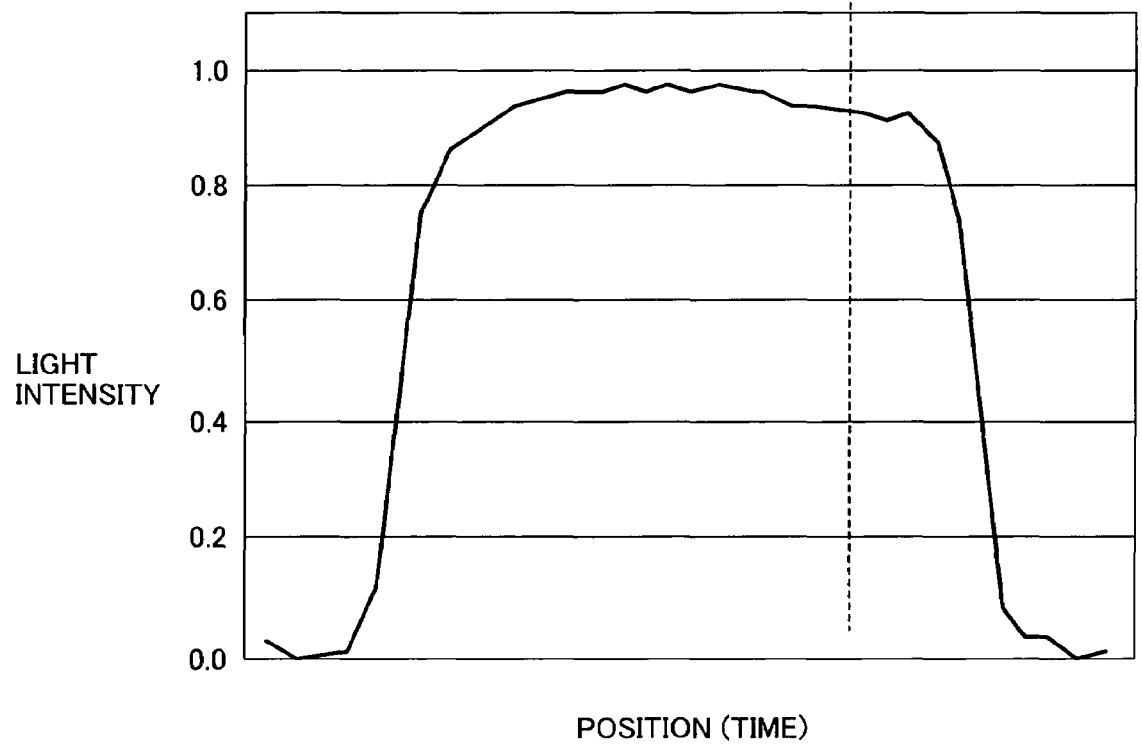
FIG. 14B shows an example of an output result of an image processing system in the case where the photomask shown in FIG. 14A is applied to a photomask defect detection apparatus in which no spatial filter is provided.

FIG. 14A shows an example of a cross-section of the photomask 4 having a construction in which a phase defect 4a is added to the photomask shown in FIG. 13A. FIG. 14B shows an output result of the image processing system 9 in the case where the photomask 4 shown in FIG. 14A is applied to the photomask defect detection apparatus in which the spatial filter 6 is not provided.

When FIGS. 13B and 14B are compared with each other, a slight difference is found in the vicinity of the phase defect 4a in FIG. 14B, but the output results each approximately agree with the calculation result shown in FIG. 7 (the light intensity is constant even in the edge portion of the phase defect 4a) Therefore, when the spatial filter 6 is not provided, it is impossible to detect the phase defect 4a based on the light intensity.

Next, an experimental result in the case where the spatial filter 6 is provided in the photomask defect detection apparatus shown in FIG. 1 will be described.

Figure 15A:
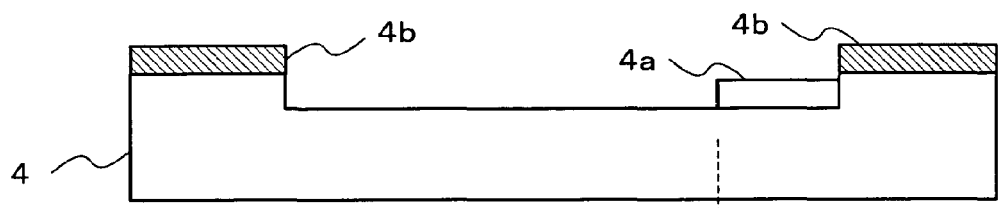
FIG. 15A shows an example of a cross section of a photomask having a construction in which a phase defect is added to the photomask shown in FIG. 13A.
Figure 15B:
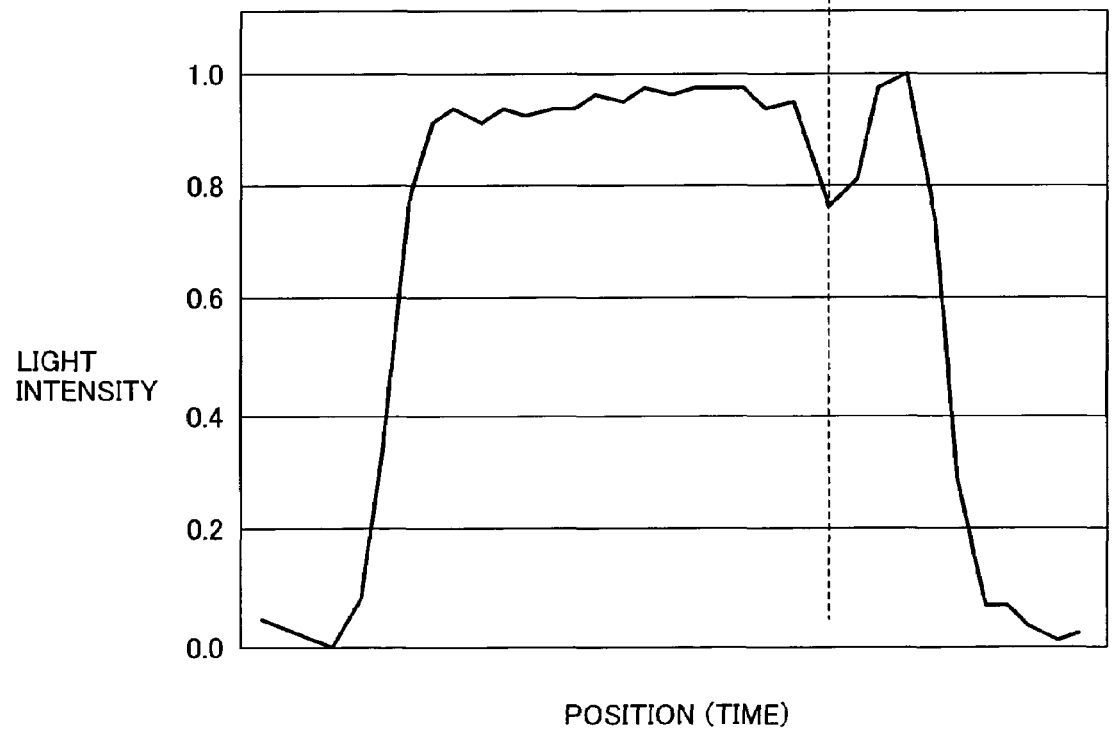
FIG. 15B shows an example of an output result of an image processing system in the case where the photomask shown in FIG. 15A is applied to a photomask defect detection apparatus in which a spatial filter is provided.

FIGS. 15A and 15B each show an example of the experimental result in the case where the spatial filter 6 is provided in the construction of the optical inspection apparatus (photomask defect detection apparatus) shown in FIG. 1.

FIG. 15A is the same as FIG. 14A. FIG. 15B shows an output result of the image processing system 9 in the case where the photomask 4 shown in FIG. 15A is applied to the photomask defect detection apparatus in which the spatial filter 6 is provided. In the detection result of the image processing system shown in FIG. 15B, the light intensity is significantly lowered in the edge portion of the phase defect 4a (the light intensity lowering portion corresponds' to the phase change information).

As described above, when the spatial filter 6 is set at the pupil position, lowering of the light intensity corresponding to the edge of the phase defect 4a appears in an image that is the detection result of the image processing system.

Therefore, by detecting the lowering of the light intensity that appears due to the spatial filter 6 provided as described above, it becomes possible to detect the phase change given by the phase defect 4a to the light beam 12 as changing of the light intensity.

Through the experiments described above, it is confirmed that the light intensity significantly lowers in the edge portion of the phase defect 4a as anticipated in the calculation results in FIGS. 10 and 11. It can be understood from comparison between the experimental results in FIGS. 14B and 15B that the spatial filter 6 has an extremely prominent effect.

By comparing the output result of the image processing system with reference data, the phase defect is identified. The reference data is, for instance, data in which phase shifter information, such as the position and shift amount of the phase shifter on the photomask, is made clear.

When phase change information (light intensity lowering portion) is contained in the output result of the image processing system and phase change information does not included in a portion of the reference data corresponding to the output result, the phase change information is regarded as a phase defect; otherwise, the phase change information is regarded as the phase shifter included according to the design.

The comparison between the output result of the image processing system and the reference data is performed in the following manner, for instance. That is, the output result of the image processing system is compared with results as to other dies containing patterns that are the same as the pattern in the photomask. Alternatively, a reference image is created from a mask pattern design database using the theoretical calculation described above and the created image is compared with the output result of the image processing system.

As described above, it becomes possible to perform the detection of the phase change information and the identification of the phase defect without being influenced by the direction and shape of the pattern on the photomask.

E. Finally, a case where another spatial filter is used will be described.

In the above description, as shown in FIG. 9, the spatial filter 6 transmits a main beam (0th-order light: a beam in the center portion) and shields a diffracted light component (beam in the peripheral portion). However, the spatial filter may have a construction as shown in FIG. 16 in which a translucent portion 6a and light-shielding portions 6b are provided in a ring zone manner.

The spatial filter 19 blocks the main beam (0th-order light) by shielding light in the center portion and transmits the diffracted light component without shielding light in the peripheral portion.

Figure 16:
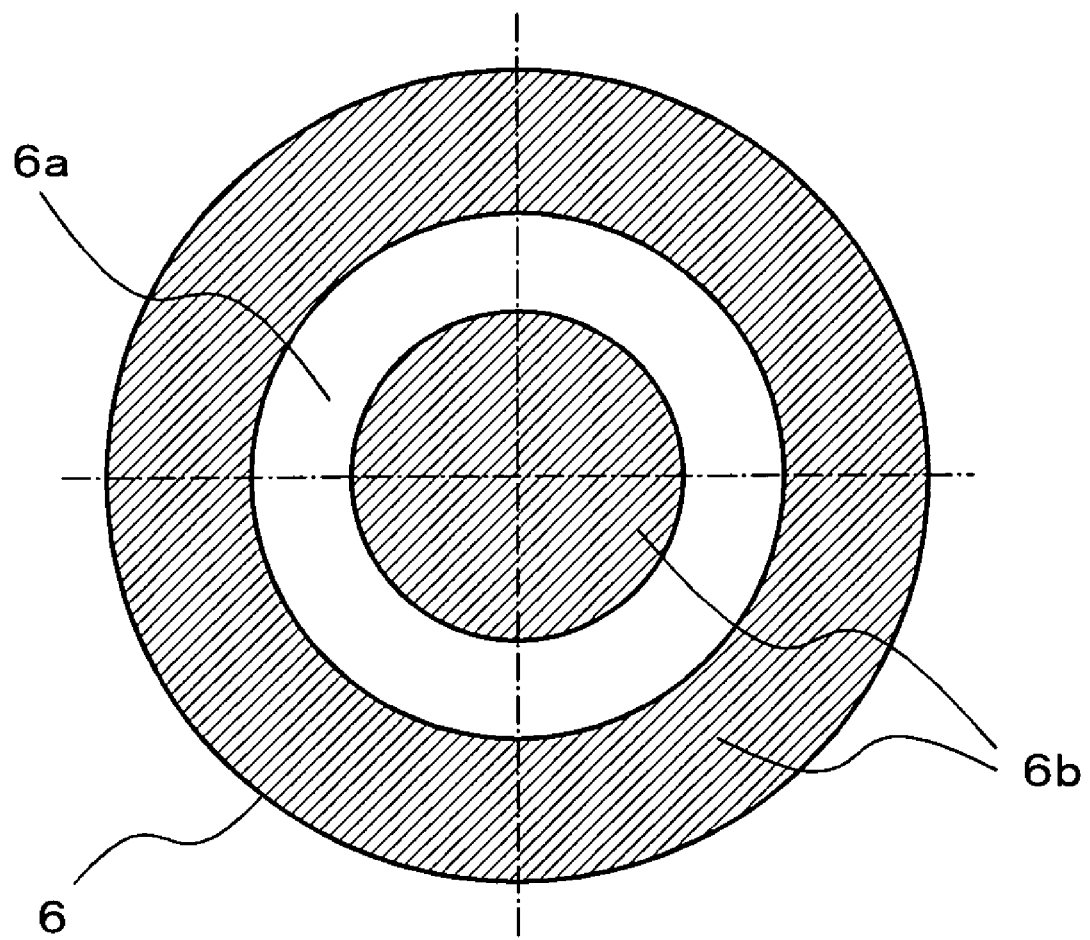
FIG. 16 shows an example of a spatial filter having a construction in which a translucent portion and light-shielding portions are provided in a ring zone manner.
Figure 17:
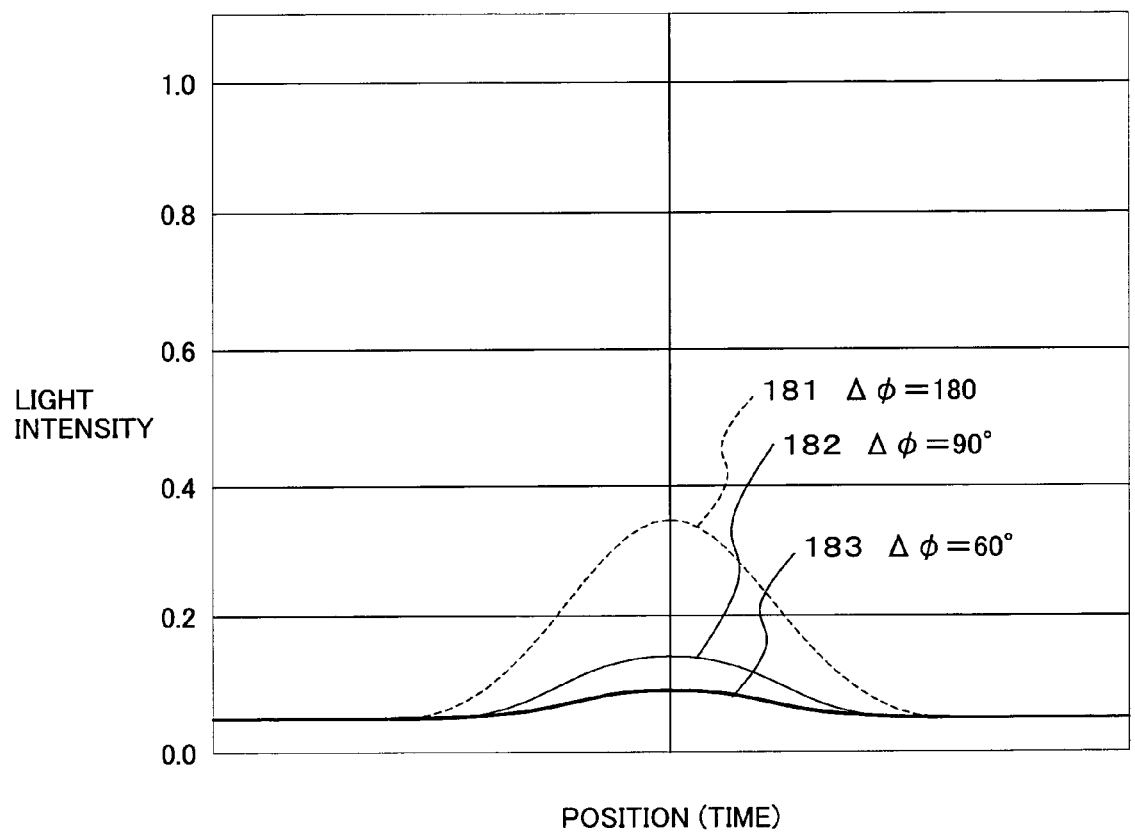
FIG. 17 shows examples of calculation results in the case where the spatial filter shown in FIG. 16 is provided in the construction of the optical inspection apparatus shown in FIG. 1 (in the case where there exists a phase defect)

FIG. 17 shows calculation results of time changes of the light intensity signal outputted by the photoelectric transducer 8 in the case where the spatial filter 19 shown in FIG. 16 is set at the pupil position existing at the rear-side focus of the collective lens 5. Here, the term "time" in the "time changes" means time corresponding to "the scanning position of the condensed spot 13".

FIG. 17 corresponds to FIG. 10 showing the calculation results of the time changes of the signal obtained by the photoelectric transducer 8 in the case where the spatial filter 6 shown in FIG. 9 is used.

When the spatial filter 19 shown in FIG. 16 is used, the light intensity for detecting the phase change information such as the phase defect is obtained in an increasing direction as shown in FIG. 17. This direction is opposite to the direction in FIG. 10.

The shape of the spatial filter is not limited to the stepped shapes in the examples shown in FIGS. 9 and 16 in which the translucent portion 6a and the light-shielding portion 6b are clearly separated from each other. For instance, an apodization filter, whose transmittance is gradually lowered toward the outside in the radial direction, may also be used. Alternatively, an ultra-high-resolution filter, whose transmittance is gradually increased toward the outside in the radial direction, may also be used. By determining the pattern shape and light transmittance of the spatial filter in this manner, it becomes possible to detect various defects of the photomask. The various defects include an isolated defect, whose defect size is approximately the same as the beam waist of the condensed beam, a defect having a periodical pattern shape, and the like. The spatial filter may be constructed using a high-density and high-integration transmission-type or reflection-type spatial modulation element that uses an LCD, a deformable mirror device (DMD), or the like and has a variable pattern.

As described above, according to the first exemplary embodiment of the present invention, light from the light source is condensed in a minute spot shape on an inspection target surface and the condensed minute-spot-shaped light is scanned onto the inspection target surface by the condensing and scanning optical system 16. Then, optical phase change information in an area of the inspection target surface irradiated with the scanned minute-spot-shaped light is detected by the phase change information detection apparatus 17. Accordingly, it is possible to identify a phase defect on the inspection target surface by comparing the detected phase change information with reference data. It is possible to perform the detection of the phase change information and the identification of the phase defect without being influenced by the direction and shape of the pattern. Therefore, according to the first exemplary embodiment of the present invention, it becomes possible to provide an optical inspection apparatus with a simple construction having a little dependence on a pattern direction and a pattern shape.

Also, the phase change information detection apparatus 17 optically Fourier-transforms light from the area of the inspection target surface irradiated with the minute-spot-shaped light and spatially filters a Fourier transformation image. The phase change information detection apparatus 17 condenses the spatially filtered light and detects the intensity of the condensed light while establishing correspondence with a scanning position. Then, the phase change information detection apparatus 17 extracts a scanning position corresponding to a portion, in which changing of the detected light intensity is found, as phase change information. Therefore, the phase change information detection apparatus 17 can detect the phase change information as changing of the light intensity.

As a result, it becomes possible to detect the phase change information with ease and at high speed, eliminating the necessity of complicated optical means and signal (image) analysis means used in the conventional technique.

In addition, the first exemplary embodiment of the present invention uses a scanning-type microscope system, so it is possible to secure high S/N that is an advantage of the scanning-type microscope system and there is little danger that a defect signal will be buried in noise.

Next, a second exemplary embodiment of the present invention will be described with reference to the drawings.

Figure 18:
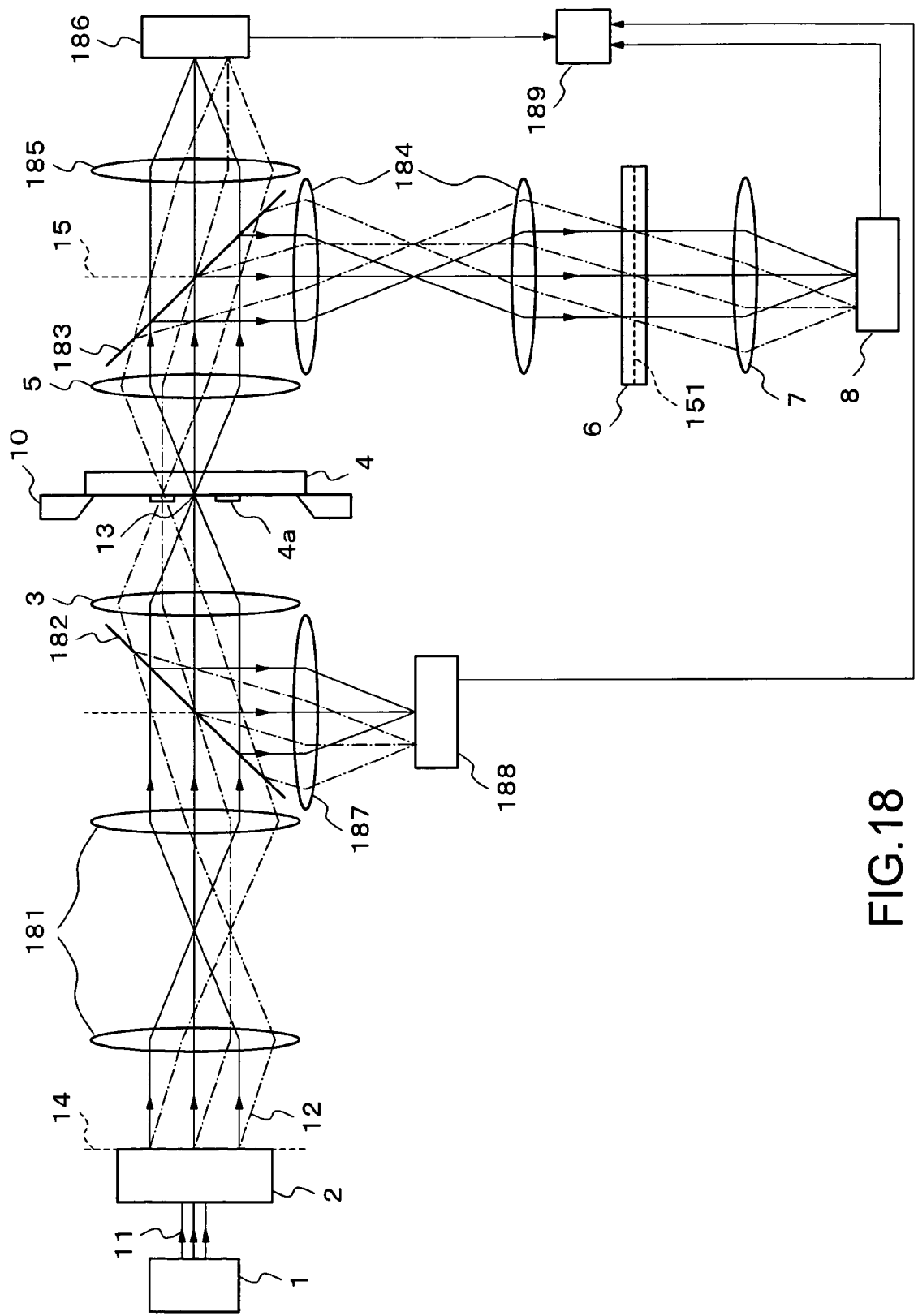
FIG. 18 shows a second exemplary embodiment of an optical inspection apparatus according to the present invention.

FIG. 18 shows an optical inspection apparatus according to the second exemplary embodiment of the present invention.

Like in the first embodiment of the optical inspection apparatus according to the present invention, the following description will be made using a photomask defect detection apparatus as an example of the optical inspection apparatus.

Each structural component that is the same as a structural component in the first embodiment shown in FIG. 1 is given the same reference symbol and the description thereof will be omitted. The second embodiment is an embodiment in which an optical system for pattern shape defect detection is added to the optical construction for phase defect detection shown in FIG. 1.

The photomask defect detection apparatus includes the following structural components in addition to the structural components in the first embodiment shown in FIG. 1. That is, the photomask defect detection apparatus includes a relay lens 181, a beam splitter 182, a beam splitter 183, a relay lens 184, and a collective lens 185. In addition, the photomask defect detection apparatus includes a photoelectric transducer 186, a collective lens 187, a photoelectric transducer 188, and an image processing system 189.

A light beam 11 emitted from a light source 1 enters a scanning optical system 2. A light beam 12 emitted from the scanning optical system 2 enters the relay lens 181. The light beam 12 emitted from the relay lens 181 transmits through the beam splitter 182 and enters an objective lens 3. The light beam 12 emitted from the objective lens 3 forms a condensed spot 13 on a surface having a pattern of a photomask 4. Accordingly, the process from the emission of the light beam 11 from the light source 1 to the formation of the condensed spot 13 on the surface of the photomask 4 is optically the same as that in the first embodiment.

The light beam 12 transmitting through the photomask 4 and condensed by a collective lens 5 is divided into two light fluxes by the beam splitter 183. As the beam splitter 183, a combination of a polarization beam splitter and a wave plate, a half mirror, or the like is used. In the construction of the second embodiment, an optical path reflected by the beam splitter 183 is used for phase defect detection. Then, a Fourier transformation surface formed at a rear-side focal position 15 of the collective lens 5 is imaged under equal-magnification on the rear side of the relay lens 184 using the relay lens 184. A phase defect is detected in the manner described in the first embodiment by providing a spatial filter 6 in a Fourier transformation surface 151 imaged in the manner described above.

Also, the light beam transmitting through the beam splitter 183 is condensed on a light reception surface of the photoelectric transducer 186 by the collective lens 185 as it is without transmitting through a spatial filter. The photoelectric transducer 186 outputs a light intensity signal in accordance with the intensity of the condensed light.

The image processing system 189 forms and outputs an image of a pattern shape of the photomask based on the position of the condensed spot 13 and the light intensity signal. It is possible to detect a defect of the pattern shape by comparing the output result and normal reference data with each other. This is pattern shape defect detection based on light transmitting through the photomask.

Also, the light beam reflected from the pattern surface of the photomask 4 passes through the objective lens 3 again to become a parallel light flux. The parallel light flux is reflected by the newly provided beam splitter 182. In this way, the light beam reflected from the pattern surface is separated.

In this embodiment, the separated reflection light from the pattern surface is condensed on the photoelectric transducer 188 by the collective lens 187 as it is. The photoelectric transducer 188 outputs a light intensity signal in accordance with the intensity of the condensed light.

The image processing system 189 forms and outputs an image of the pattern shape of the photomask based on the position of the condensed spot 13 and the light intensity signal. It is possible to detect a defect of the pattern shape by comparing the output result and the normal reference data with each other. This is pattern shape defect detection based on light reflected by the photomask.

Here, it is also possible to perform phase defect detection based on reflection light by further separating the reflection light of the pattern surface of the photomask 4 and providing a spatial filter in the separated optical path. This is the same as the phase defect detection based on transmitted light of the pattern surface of the photomask 4. In the case of the phase defect detection based on reflection light, however, a round-trip phase difference due to reflection from the upper surface or lower surface of the substrate occurs in the portion of the phase defect. Therefore, a situation is different from the case of the phase defect detection based on transmitted light, so some consideration is needed.

As described above, with the construction described in the second embodiment, it becomes possible to simultaneously perform ordinary pattern shape defect detection in addition to phase mask defect detection. Therefore, it becomes possible to simultaneously detect respective defects (pattern shape defect, phase defect) with respect to a photomask for which both of a light-shielding pattern and a phase shifter are provided.

Also, the same defect signal as in the case of conventional pattern shape defect inspection is obtained, so it is possible to divert a conventional algorithm for defect detection.

The above description has been made by taking the Alt-PSM as an example of the phase-shift mask, but it is also expected that the same effect will be obtained even in the case of an attenuated film or a substance other than a thin film with which phase changing occurs. That is, it is expected that the same effect will be obtained even in such cases as halftone film defect detection about an Att-PSM in the case of transmission-type defect detection, and foreign matter defect detection in the case of reflection-type defect detection.

The embodiments of the present invention described above relate to a technique of detecting a defect of a photomask, but the present invention is also applicable to detection of a defect of a surface state of an electron device or the like having a fine pattern.

While the present invention has been described in connection with certain preferred embodiments, it is to be understood that the subject matter encompassed by the present invention is not limited to those specific embodiments. On the contrary, it is intended to include all alternatives, modifications, and equivalents as can be included within the spirit and scope of the following claims.

Additionally, it is the inventor's intent to retain all equivalents of the claimed invention even if the claims are amended during prosecution.

What is claimed is:

1. An optical inspection apparatus for inspecting an inspection target surface by irradiating the inspection target surface with light, comprising:
    a condensing and scanning optical system for condensing light from a light source on the inspection target surface in a minute spot shape and scanning the condensed minute-spot-shaped light onto the inspection target surface, said optical system comprising a collective lens that forms a parallel light flux from the condensed minute-spot-shaped light such that the parallel light flux forms a Fourier transformation image; and
    a phase change information detection apparatus for detecting optical phase change information in an area of the inspection target surface irradiated with the minute-spot-shaped light scanned by the condensing and scanning optical system.

2. An optical inspection apparatus according to claim 1, wherein the phase change information detection apparatus detects the phase change information as changing of light intensity.

3. An optical inspection apparatus according to claim 1, wherein the phase change information detection apparatus detects a phase defect by comparing the detected phase change information with reference data that clarifies information about a phase shifter on the inspection target surface.

4. An optical inspection apparatus according to claim 1, wherein the phase change information detection apparatus includes:
    a Fourier transformation apparatus for optically Fourier-transforming light from the area of the inspection target surface irradiated with the minute-spot-shaped light;
    a spatial filter for spatially filtering the Fourier transformation image obtained as a result of the Fourier-transforming by the Fourier transformation apparatus; and
    a phase change information extraction apparatus for extracting the phase change information on the inspection target surface based on light spatially filtered by the spatial filter.

5. An optical inspection apparatus according to claim 4, wherein the phase change information extraction apparatus condenses the spatially filtered light, detects the intensity of the condensed light while establishing correspondence with a scanning position, and extracts a scanning position corresponding to a portion, in which changing of the detected light intensity is found, as the phase change information.

6. An optical inspection apparatus according to claim 4, wherein a pattern shape of the spatial filter is determined based on a difference between (i) the Fourier transformation image at a boundary between the area of the inspection target surface having property, with which optical phase changing occurs, and the area thereof not having the property and (ii) the Fourier transformation image in the area not having the property.

7. An optical inspection apparatus according to claim 4, wherein the light from the area of the inspection target surface irradiated with the minute-spot-shaped light is light transmitting through the area.

8. An optical inspection apparatus according to claim 4, wherein the light from the area of the inspection target surface irradiated with the minute-spot-shaped light is light reflected from the area.

9. An optical inspection apparatus according to claim 1, wherein the inspection target surface is a surface of a reticle and the phase change information is edge position information of a tight transmitting pattern formed on the reticle.

10. An optical inspection apparatus according to claim 1, wherein the inspection target surface is a surface of an electronic component substrate and the phase change information is edge position information of a light transmitting pattern formed on the electronic component substrate.

11. An optical inspection apparatus according to claim 1, further comprising an amplitude information detection apparatus for detecting optical amplitude information in the area of the inspection target surface irradiated with the minute-spot-shaped light scanned by the condensing and scanning optical system.

12. An optical inspection apparatus according to claim 11, wherein the amplitude information detection apparatus condenses light from the area of the inspection target surface irradiated with the minute-spot-shaped light and sets intensity of the condensed light as the amplitude information in the area.

13. An optical inspection apparatus according to claim 11, wherein the inspection target surface is one of a surface of a reticle and a surface of an electronic component substrate.

14. An optical inspection method for inspecting an inspection target surface by irradiating the inspection target surface with light, comprising:
  condensing light from a light source on the inspection target surface in a minute spot shape;
  scanning the condensed minute-spot-shaped light onto the inspection target surface;
  using a parallel light flux, formed from the condensed minute-spot-shaped light in a collective lens, to form a Fourier transformation image; and
  detecting optical phase change information in an area of the inspection target surface irradiated with the scanned minute-spot-shaped light.

15. An optical inspection method according to claim 14, wherein the phase change information is detected as light intensity changing.

16. An optical inspection method according to claim 14, wherein a phase defect is detected by comparing the detected phase change information with reference data that clarifies information about a phase shifter on the inspection target surface.

17. An optical inspection method according to claim 14, wherein the detecting of the optical phase change information in the area of the inspection target surface irradiated with the scanned minute-spot-shaped light includes:
  optically Fourier-transforming light from the area of the inspection target surface irradiated with the minute-spot-shaped light;
  spatially filtering a Fourier transformation image obtained as a result of the Fourier transforming; and
  extracting the phase change information on the inspection target surface based on spatially filtered light.

18. An optical inspection method according to claim 17, wherein the extracting of the phase change information on the inspection target surface based on the spatially filtered light includes:
  condensing the spatially filtered light;
  detecting the intensity of the condensed light while establishing correspondence with a scanning position; and
  extracting a scanning position corresponding to a portion, in which changing of the detected light intensity is found, as the phase change information.

19. An optical inspection method according to claim 17, wherein a pattern shape of a spatial filter doing the spatially filtering is determined based on a difference between (i) the Fourier transformation image at a boundary between the area of the inspection target surface having property, with which optical phase changing occurs, and the area thereof not having the property and (ii) the Fourier transformation image in the area not having the property.

20. An optical inspection method according to claim 17, wherein the light from the area of the inspection target surface irradiated with the minute-spot-shaped light is light transmitting through the area.

21. An optical inspection method according to claim 17, wherein the light from the area of the inspection target surface irradiated with the minute-spot-shaped light is light reflected from the area.

22. An optical inspection method according to claim 14, wherein the inspection target surface is a surface of a reticle and the phase change information is edge position information of a light transmitting pattern formed on the reticle.

23. An optical inspection method according to claim 14, wherein the inspection target surface is a surface of an electronic component substrate and the phase change information is edge position information of a light transmitting pattern formed on the electronic component substrate.

24. An optical inspection method according to claim 14, further comprising detecting optical amplitude information in the area of the inspection target surface irradiated with the scanned minute-spot-shaped light.

25. An optical inspection method according to claim 24, further comprising:
  condensing light from the area of the inspection target surface irradiated with the minute-spot-shaped light; and
  setting intensity of the condensed light as the amplitude information in the area.

26. An optical inspection method according to claim 24, wherein the inspection target surface is one of a surface of a reticle and a surface of an electronic component substrate.

27. A method of optical inspection comprising:
  forming a minute condensed spot on an inspection target using a condensed light beam formed in a scanning optical system and an objective lens such that the minute condensed spot is scanned on the inspection surface and the condensed light beam is transmitted through the inspection surface to a collective lens;
  using a parallel light flux, formed from the condensed light beam in the collective lens, to form a Fourier transformation image at a rear-side focal position of the collective lens, the image and the condensed light beam filtered spatially;
  transmitting the condensed light beam to a photoelectric transducer; and
  converting an intensity of the condensed light beam into an electric signal that is sent to an image processing system to compare detected phase change information with reference data that clarified information about a phase shifter on the inspection target.

28. The method according to claim 27, wherein the minute condensed spot comprises a diameter that is greater than or equal to 0.3 µm and less than or equal to 0.4 µm.

* * * * *